United States Patent
Suschek

(10) Patent No.: US 10,022,527 B2
(45) Date of Patent: Jul. 17, 2018

(54) IMMERSION DEVICE

(71) Applicant: BSN medical GmbH, Hamburg (DE)

(72) Inventor: Christoph V. Suschek, Langenfeld (DE)

(73) Assignee: BSN Medical GmbH, Hamburg (DE)

( * ) Notice: Subject to any disclaimer, the term of this patent is extended or adjusted under 35 U.S.C. 154(b) by 292 days.

(21) Appl. No.: 15/030,865

(22) PCT Filed: Oct. 24, 2014

(86) PCT No.: PCT/EP2014/072844
§ 371 (c)(1),
(2) Date: Jun. 8, 2016

(87) PCT Pub. No.: WO2015/059273
PCT Pub. Date: Apr. 30, 2015

(65) Prior Publication Data
US 2016/0296738 A1 Oct. 13, 2016

(30) Foreign Application Priority Data

Oct. 24, 2013 (DE) .................. 10 2013 017 524

(51) Int. Cl.
| | |
|---|---|
| *A61M 35/00* | (2006.01) |
| *A61H 33/14* | (2006.01) |
| *A61H 35/00* | (2006.01) |
| *A61K 9/00* | (2006.01) |
| *A61H 33/04* | (2006.01) |

(52) U.S. Cl.
CPC ............. *A61M 35/00* (2013.01); *A61H 33/14* (2013.01); *A61H 35/00* (2013.01); *A61H 35/006* (2013.01); *A61K 9/0009* (2013.01); *A61H 2033/048* (2013.01); *A61H 2230/255* (2013.01); *A61H 2230/505* (2013.01); *A61M 2202/0275* (2013.01); *A61M 2205/12* (2013.01); *A61M 2205/36* (2013.01); *A61M 2210/08* (2013.01)

(58) Field of Classification Search
CPC ....... A61M 35/00; A61H 33/14; A61H 35/00; A61H 35/006; A61K 9/0009
See application file for complete search history.

(56) References Cited

U.S. PATENT DOCUMENTS

| | | | |
|---|---|---|---|
| 8,017,074 B2 * | 9/2011 | Arnold ................. | A61L 2/0094 422/28 |
| 2009/0108777 A1 * | 4/2009 | Hyde ................... | A61K 9/7084 315/307 |

(Continued)

OTHER PUBLICATIONS

K.D. Kroncke, K. Fehsel & V. Kolb-Bachofen: "Includible Nitric Oxide Synthase in Human Diseases", Clinical and Experimental Immunology, (1998), pp. 147-156, vol. 113, Blackwell Science LTD.,Germany.

(Continued)

*Primary Examiner* — Tatyana Zalukaeva
*Assistant Examiner* — Kai Weng
(74) *Attorney, Agent, or Firm* — Rankin, Hill & Clark LLP

(57) ABSTRACT

The invention relates to an immersion device comprising a nitrogen monoxide generating unit and a volume unit provided for immersing objects. The invention also relates to the use of said device for treating diseases, in particular chronic wounds and diabetes, and also to blood flow impairments associated with blood vessel disorders.

10 Claims, 6 Drawing Sheets

(56) References Cited

U.S. PATENT DOCUMENTS

Figure 1:
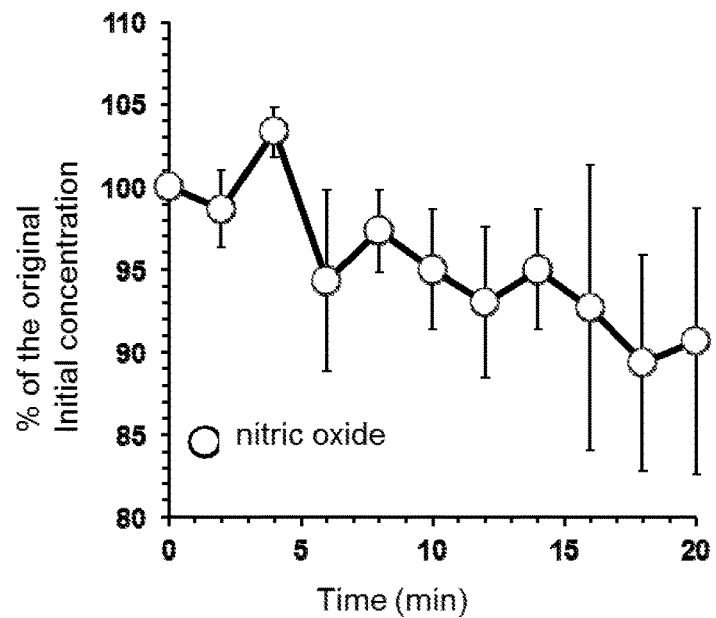
Figure 1:
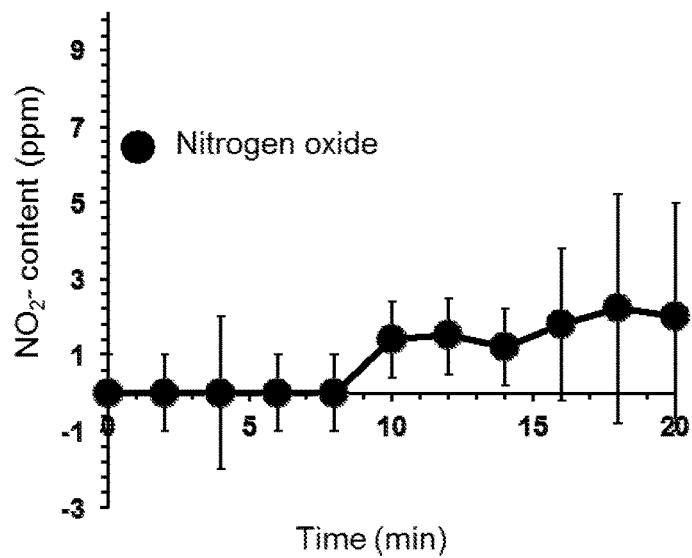

| | | | | |
|---|---|---|---|---|
| 2011/0033437 | A1* | 2/2011 | Smith | A61K 9/0014 424/94.1 |
| 2012/0065576 | A1* | 3/2012 | Stryker | A61H 9/005 604/20 |

OTHER PUBLICATIONS

K. Matsunaga & R. F. Furchgott: "Responses of Rabbit Aorta to Nitric Oxide and Superoxide Generated by Ultraviolet Irradiation of Solutions Containing Inorganic Nitrite", The Journal of Pharmacology and Experimental Therapeutics, (1991), pp. 1140-1146, vol. 259, The American Society for Pharmacology and Experimental Therapeutics, United States.

M. Fischer & P. Warneck: "Photodecomposition of Nitrite and Undissociated Nitrous Acid in Aqueous Solution", Journal of Physical Chemistry, (1996), pp. 18749-18756, vol. 100, American Chemical Society, United States.

H. Strehlow & I. Wagner: "Flash Photolysis in Aqueous Nitrite Solutions", Zeitschrift fur Physikalische Chemie Neue Folge, (1982), pp. 151-160, vol. 132, Akademische Verlagsgesellschaft, Wiesbaden.

S. Frank, H. Kampfer, C. Wetzler, & J. Pfeilschifter: "Nitric Oxide Drive Skin Repair: Novel Functions of an Established Mediator", Kidney International, (2002), pp. 882-888, vol. 61, International Society of Nephrology, United States.

S. Frank, B. Stallmeyer, H. Kampfer, N. Kolb, & J. Pfeilschifter: "Nitric Oxide Triggers Enhanced Induction of Vascular Endothelial Growth Factor Expression in Cultured Keratinocytes (HaCaT) and During Cutaneous Wound Repair", The FASEB Journal, (1999), pp. 2002-2014, vol. 13, Federation of American Societies for Experimental Biology, United States.

S. Frank, H. Kampfer, M. Podda, R. Kaufmann & J. Pfeilschifter: "Identification of Copper/Zinc Superoxide Dismutase as a Nitric Oxide-Regulated Gene in Human (HaCaT) Keratinocytes: Implications for Keratinocyte Proliferation", Biochemical Journal, (2002), pp. 719-728, vol. 346, Biochemical Society, Great Britian.

K. Yamasaki, H. D.J. Edington, C. McClosky, E. Tzeng, A. Lizonova, I. Kovesdi, D. L. Steed, & Timothy R. Billiar: "Reversal of Impaired Wound Repair in iNOS-deficient Mice by Topical Adenoviral-mediated INOS Gene Transfer", The Journal of Clinical Investigation, (1998), pp. 967-971, vol. 101, The American Society for Clinical Investigation Inc., United States.

J. Pfeilschifter, W. Eberhardt & A. Huwiler: "Nitric Oxide and Mechanisms of Redox Signalling: Matrix and Matrix-Metabolizing Enzymes as Prime Nitric Oxide Targets", European Journal of Pharmacology, (2001), pp. 279-286, vol. 429, Elsevier Science B.V., Amsterdam, The Netherlands.

Y. Ishii, T. Ogura, M. Tatemichi, H. Fujisawa, F. Otsuka, & H. Esumi:"Induction of Matrix Metalloproteinase Gene Transcription by Nitric Oxide and Mechanisms of MMP-1 Gene Induction in Human Melanoma Cell Lines", Internal Journal of Cancer, (2003), pp. 161-168, vol. 103, Wiley-Liss, Inc.

M.B. Witte, F.J. Thornton, D.T. Efron, & A. Barbul: "Enhancement of Fibroblast Collagen Synthesis by Nitric Oxide", Nitric Oxide: Biology and Chemistry, (2000), pp. 572-582, vol. 4, Academic Press, United States.

F. Verrecchia & A. Mauviel: "TGF-beta and TNF-alpha: Antagonistic Cytokines Controlling Type I Collagen Gene Expression", Cellular Signalling, (2004), pp. 873-880, vol. 16, Elsevier Inc., Amsterdam, The Netherlands.

D.A. Siwik & W.S. Colucci: "Regulation of Matrix Metalloproteinases by Cytokines and Reactive Oxygen/Nitrogen Species in the Myocardium", Heart Failure Review, (2004), pp. 43-51, vol. 9, Kluwer Academic Publishers, The Netherlands.

V.M. Darley-Usmar, R.P. Patel, V.B. O'Donnell & B.A. Freeman: "Antioxidant Actions of Nitric Oxide", Nitric Oxide: Biology and Pathobiology, (2000), pp. 265-276, Academic Press, San Diego. (Ed.).

S. P. Goss, B. Kalyanaraman & N. Hogg: "Antioxidant Effects of Nitric Oxide and Nitric Oxide Donor Compounds on Low-Density Lipoprotein Oxidation", Methods in Enzymology, (1999), pp. 444-453, vol. 301, Academic Press, United States.

D.A. Wink, J.A. Cook, R. Pacelli, J. Liebmann, M.C. Krishna & J.B. Mitchell: "Nitric Oxide (NO) Protects Against Cellular Damage by Reactive Oxygen Species", Toxicology Letters, (1995), pp. 221-226, vol. 82/83, Elsiever Science Ireland Ltd., Ireland.

B. Brüne, A. von Knethen & K.B. Sandru: "Nitric Oxide (NO): An Effector of Apoptosis", Cell Death & Differentiation, (1999), pp. 969-975, vol. 6, Stockton Press, United Kingdom.

D. Moellering, J. McAndrew, R.P. Patel, T. Cornwell, T. Lincoln, X. Cao, J.L. Messina, H.J. Forman, H. Jo, & V.M. Darley-Usmar: "Nitric Oxide-Dependent Induction of Glutathione Synthesis through Increased Expression of Gamma-Glutamylcysteine Synthetase", Archives of Biochemistry and Biophysics, (1998), pp. 74-82, vol. 358, Academic Press, United States.

U. Förstermann, M. Nakane, W.R. Tracey & J.S. Pollock: "Isoforms of Nitric Oxide Synthase: Functions in the Cardiovascular System", European Heart Journal Supp I, (1993), pp. 10-15, vol. 14, Oxford University Press, Great Britain.

P. He, M. Zeng & F.E. Curry: "Effect of Nitric Oxide Synthase Inhibitors on Basal Microvessel Permeability and Endothelial Cell [Ca2+]i", American Journal of Physiology, (1997), pp. H747-H755, vol. 273, American Physiological Society, United States.

M. Toborek & S. Kaiser: "Endothelial Cell Functions. Relationship to Atherogenesis", Basic Research in Cardiology, (1999), pp. 295-314, vol. 94, Steinkopff Verlag, Germany.

M. Kelm & B. Strauer: "Endotheliale Dysfunktion Therapeutische and prognostische Relevanz", Der Internist, (1999), pp. 1300-1307, vol. 40, Springer-Verlad, Germany.

T.P. Amadeu, A.B. Seabra, M.G. de Oliveira & A.M. Costa: "S-nitrosoglutathione-Containing Hydrogel Accelerates Rat Cutaneous Wound Repair", Journal of the European Academy of Dermatology and Venereology, (2007), pp. 629-637, vol. 21, European Academy of Dermatology and Venereology, Switzerland.

R. Weller & M.J. Finnen: "The Effects of Topical Treatment with Acidified Nitrite on Wound Healing in Normal and Diabetic Mice", Nitric Oxide, (2006), pp. 395-399, vol. 15, Elsevier Inc., Amsterdam, The Netherlands.

A.B. Shekhter, V.A. Serezhenkov, T.G. Rudenko, A.V. Pekshev, & A.F. Vanin: "Beneficial Effect of Gaseous Nitric Oxide on the Healing of Skin Wounds", Nitric Oxide, (2005), pp. 210-219, vol. 12, Elsevier Inc., Amsterdam, The Netherlands.

W.S. McDonald, T.P. Lo, Jr., M. Thurmond, C. Jones, R. Cohen, A. Miller & D. Beasley: "Role of Nitric Oxide in Skin Flap Delay", Plastic and Reconstructive Surgery, (2004), pp. 927-931, vol. 113, American Society of Plastic Surgeons, United States.

C. Belge, P.B. Massion, M. Pelat, & J.L. Balligand: "Nitric Oxide and the Heart: Update on New Paradigms", Annals of the New York Academy of Science, (2005), pp. 173-182, vol. 1047, New York Academy of Sciences, United States.

B. Gaston: "Summary: Systemic Effects of Inhaled Nitric Oxide", Proceeding of the American Thoracic Society, (2006), pp. 170-172, vol. 3, American Thoracic Society, United States.

T.M. Dawson & S.H. Snyder: "Gases as Biological Messengers: Nitric Oxide and Carbon Monoxide in the Brain", The Journal of Neuroscience, (1994) pp. 5147-5159, vol. 14, Society of Neuroscience, United States.

C.C. Miller, M.K. Miller, A. Ghaffari & B. Kunimoto: "Treatment of Chronic Nonhealing Leg Ulceration with Gaseous Nitric Oxide: A Case Study", Journal of Cutaneous Medicine and Surgery, (2004), pp. 233-238, vol. 8, Canadian Dermatology Association, Canada.

A. Ghaffari, D.H. Neil, A. Ardakani, J. Road, A. Ghahary & C.C. Miller: "A Direct Nitric Oxide Gas Delivery System for Bacterial and Mammalian Cell Cultures", Nitric Oxide, (2005), pp. 129-140, vol. 12, Elsevier Inc., Amsterdam, The Netherlands.

A. Ghaffari, C.C. Miller, B. McMullin & A. Ghahary: "Potential Application of Gaseous Nitric Oxide as a Topical Antimicrobial Agent", Nitric Oxide, (2006), pp. 21-29, vol. 14, Elsevier Inc., Amsterdam, The Netherlands.

A. Ghaffari, R. Jalili, M. Ghaffari, C. Miller & A. Ghahary: "Efficacy of Gaseous Nitric Oxide in The Treatment of Skin and

(56) References Cited

OTHER PUBLICATIONS

Soft Tissue Infections", Wound Repair and Regeneration, (2007), pp. 368-377, vol. 15, Wound Healing Society, United States.

Z.S. Galis & J.J. Khatri: "Matrix Metalloproteinases in Vascular Remodeling and Atherogenesis: The Good, the Bad, and the Ugly", Circulation Research, (2002), pp. 251-262, vol. 90, American Heart Association Inc., United States.

S.C. Tyagi & M.R. Hayden: "Role of Nitric Oxide in Matrix Remodeling in Diabetes and Heart Failure", Heart Failure Reviews, (2003), pp. 23-28, vol. 8, Kluwer Academic Publishers, The Netherlands.

J. Pfeilschifter, W. Eberhardt & K.F. Beck: "Regulation of Gene Expression by Nitric Oxide", Pflagers Archives—European Journal of Physiology, (2001), pp. 479-486, vol. 442, Springer-Verlag, Germany.

R. Zamora, Y. Vodovotz, K.S. Aulak, P.K. Kim, J.M. Kane, III, L. Alacron, D.J. Stuehr & T.R. Billiar: "A DNA Microarray Study of Nitric Oxide-induced Genes in Mouse Hepatocytes: Implications for Hepatic Heme Dxygenase-1 Expression in Ischemia/Reperfusion", Nitric Oxide, (2002), pp. 165-186, vol. 7, Elsevier Science (USA), United States.

J. Hemish, N. Nakaya, V. Mittal & G. Enikolopov: "Nitric Oxide Activates Diverse Signaling Pathways to Regulate Gene Expression", The Journal of Biological Chemistry, (2003), pp. 42321-42329, vol. 278, The American Society for Biochemistry and Molecular Biology Inc., United States.

M. Ziche, L. Morbidelli, E. Masini, S. Amerini, H.J. Granger, C.A. Maggi, P. Geppetti & F. Ledda: "Nitric Oxide Mediates Angiogenesis in Vivo and Endothelial Cell Growth and Migration in Vitro Promoted by Substance P", The Journal of Clinical Investigation, (1994), pp. 2036-2044, vol. 94, The American Society for Clinical Investigation Inc., United States.

S.J. Leibovich, P.J. Polverini, T.W. Fong, L.A. Harlow & A.E. Koch: "Production of Angiogenic Activity by Human Monocytes Requires an L-Arginine/Nitric Oxide-Synthase-Dependent Effector Mechanism", Journal of Cell Biology, (1994), pp. 4190-4194, vol. 91, The Proceedings of the National Academy of Sciences, United States.

N.S. Bryan, B.O. Fernandez, S.M. Bauer, M.F. Garcia-Saura, A.B. Milsom, T. Rassaf, R.E. Maloney A. Bharti, J. Rodriguez & M. Feelisch: "Nitrite is a Signaling Molecule and Regulator of Gene Expression in Mammalian Tissues", Nature Chemical Biology, (2005), pp. 290-297, vol. 1, Nature Publishing Group, USA.

U. Förstermann & W.C. Sessa: "Nitric Oxide Synthases: Regulation and Function", European Heart Journal, (2012), pp. 829-837, vol. 33, Oxford University Press, Great Britain.

I Wagner, H. Strehlow & G. Busse: "Flash Photolysis of Nitrate Ions in Aqueous Solution", Zeitschrift fur Physikalische Chemie Neue Folge, (1980), pp. 1-33, vol. 123, Akademische Verlagsgesellschaft, Wiesbaden.

\* cited by examiner

A

B

IMMERSION DEVICE

The present invention relates to an immersion device comprising a nitric oxide-generating unit as well as a volume unit provided for purposes of immersing objects, and it also relates to the use of this device for treating diseases, especially chronic wounds, and impaired perfusion associated with diabetes and vascular disease.

The treatment of impaired perfusion and of the resultant chronic wounds remains inadequate in day-to-day clinical practice. These ailments are not only a serious medical problem, but also an economic problem. For instance, it is estimated that, in Germany alone, some 2.4 million diabetics suffer from impaired perfusion and/or inadequate wound healing. This hampers the quality of life of those affected and they endure avoidable pain. The annual treatment costs are estimated at 3 billion euros. As the population ages, far more people will experience such poorly healing wounds in the future. In fact, estimates indicate that these numbers will have doubled by the year 2025.

Current therapeutic approaches are primarily based on the moderately effective pharmacological support of tissue perfusion as well as on insufficient support in the form of wound dressing systems for the healing of chronic wounds.

An important significant physiological principle of the human skin is the enzymatic production of nitric oxide by enzymes from the family of the NO synthases, which can be synthesized by all types of cells [1]. The substrate of the NO synthases is the amino acid L-arginine. A distinction is made nowadays between two constitutively expressed and one inducible isoform of the NO synthases. The constitutively expressed NO synthases include the primarily neuronally localized NO synthase (nNOS) and the primarily endothelially localized NO synthase (eNOS) which, however, is also expressed in dermal fibroblasts and in the musculocutaneous flap, whereas the inducible isoform, the iNOS, is only induced by the effect of proinflammatory stimuli and, in contrast to the constitutive isoforms, can produce locally high concentrations of NO over a prolonged period of time (days).

Below, the terms nitrogen monoxide, nitric oxide, nitric oxide radical, NO and NO' will be employed as equivalent terms for the same molecule.

In addition, NO can also be released non-enzymatically from nitrite or nitrosothiols. The non-enzymatic generation of NO takes place under acidic and reducing conditions. In this process, NO is released, for example, from nitrite.

This reaction is physiologically significant in the acidic environment of the stomach as well as of the skin. It is also known that UVA light can release from nitrite a substance having the physiological properties of NO [2]. In fact, it has been demonstrated that NO can be formed from nitrite through the modality of photodecomposition [3; 4].

Within the scope of inflammatory processes of the skin and in an interaction of the various cell systems, NO regulates, among other things, the proliferation and the differentiation of skin cells and thus, for instance, also wound healing [5]. A number of genes have been identified as being dominantly NO-regulated in wound-healing processes of the skin [6; 7], and accordingly, wound healing in iNOS-deficient mice has been found to be a significantly delayed process [8]. Other genes that are under the transcription control by NO are protectively active stress-protection genes such as heat-shock proteins, chaperones or also heme oxygenase-1. Other NO-regulated genes serve either to counter-regulate inflammatory reactions or to repair local damage (this especially includes many members of the family of matrix metalloproteinases (MMP)). NO can influence the gene expression of the MMPs, and also their physiological inhibitors, the tissue inhibitors of matrix proteinases (TIMP) and besides, NO can modulate their activity by means of nitrosation, thus countering greater collagen breakdown by the MMPs [9]. In addition, NO also influences the expression and activity of growth factors such as, for instance, the VEGF [37; 38]. Thus, NO donors were able to stimulate, for example, angiogenesis which, along with collagen synthesis, is a key element in wound healing [39], whereby NO in keratinocytes and macrophages is capable of inducing the synthesis of the angiogenesis factor VEGF [5; 40].

Furthermore, experiments with exogenic NO donors have shown that NO leads to a significant increase in collagen synthesis in fibroblasts [10; 11]. An important physiological inductor of the synthesis of new collagen is the transforming growth factor-β (TGF-β), in contrast to which interleukin-1 (IL-1), IL-6, TNF-α as well as reactive oxygen species (ROS) can significantly reduce or even inhibit the synthesis of new collagen [12; 13]. Owing to its capability to react with other radicals and to thus eliminate them, NO can also have a protective effect [14]. For instance, NO is able to protect against DNA damage induced by hydroxyl radicals as well as against cell death induced by $H_2O_2$, and it also has a greater capacity than vitamin E to terminate radical-induced lipid peroxidation [15; 16].

In addition, numerous other protective properties of NO are described. Thus, NO is said to protect against hypoxia-induced damage, it develops hepatocyte-protective and neuro-protective effects and can also protect against apoptosis by inactivating effector caspases [17]. Moreover, already at low concentrations, NO can modulate important components of antioxidative protection such as, for example, glutathione metabolism (GSH) in that it induces an increase in the expression of the two key enzymes of GSH synthesis, namely, γ-glutamyl-cysteine synthetase (γ-GCS) and γ-glutamyl transpeptidase [18].

Once it has been formed, NO easily diffuses into the vessel wall as well as into the vessel lumen, and it is involved, for instance, in the regulation of thrombocyte adhesion and thrombocyte aggregation, of vascular rolling and of the transmigration of neutrophilic granulocytes and monocytes, as well as of endothelial permeability [20]. NO also relaxes the smooth muscle cells in the vessel wall by activating the soluble guanylate cyclase, the key enzyme in the regulation of blood pressure. Therefore, the endothelially formed NO is of essential significance for maintaining vascular function as well as vascular structure, thus essentially influencing hemodynamic parameters, especially blood pressure, but also tissue-ischemic conditions [21; 22].

In the case of a reduced NO synthesis rate, animal models have shown a delay in the formation of new vessels and in wound healing as well as a greatly impaired re-epithelization of skin wounds due to a reduced proliferation rate of the keratinocytes. As a transmitter of vascular relaxation, NO can increase the blood flow rate in the wound area, thus leading to a greater supply of oxygen and nutrients as well as to improved cellular infiltration of the tissue [5].

The topical treatment of wounds with NO donors during the early phase of cutaneous wound healing translates into a significantly accelerated wound closure and re-epithelization in rats [23] as well as into improved wound healing in mice with a diabetic background [24]. The daily topical exposure of wounds to air-plasma containing NO significantly improved wound healing of septic as well as aseptic wounds in rat models [25]. In spite of numerous indications of the positive effect of NO on wound healing, up until now, there has been only one documented pilot study in humans, namely, a study involving a 55 year-old patient in whom an NO gas therapy led to the complete healing of an *Ulcus crurius venosum* on the foot which had been resistant to therapy for several years [26]. Through the breakdown of reactive oxygen species, exogenically administered NO can diminish damage caused by ischemia or reperfusion and can considerably improve the microcirculation of skin tissue. These properties play a special role in the revitalization of edge zones of free skin flap plastic surgery within the scope of soft-tissue coverings [26].

Current therapeutic approaches relating to the NO balance primarily attempt to address the NO-induced cGMP-dependent signal cascade. Therapeutic approaches aimed at directly influencing NO availability in the organism are limited to the use of organic nitrites and nitrates [27]. In clinical practice so far, NO gas has only been employed as an inhalation therapy in the treatment of various acute pulmonary dysfunctions, whereby experimental studies have also demonstrated a systemic effect of inhaled NO [28]. The diffusion coefficient of NO at 37° C. [98.6° F.] is approximately 1.4 higher than that of oxygen or carbon monoxide, on which basis the diffusion path that can be achieved in the tissues was calculated to be 500 μm [29].

Ghaffari et al. were able to demonstrate significant antibacterial effects and thus the relevance of exogenic NO gas in the treatment of bacteria-infected wounds and burn injuries as well as of non-healing wounds [31; 32], whereby the NO concentrations employed in vitro did not display any toxic effects on human fibroblasts, keratinocytes or endothelial cells [33].

In summary, nitric oxide (NO) has proven to be a physiological important bioactive molecule. Owing to its dilating effect on blood vessels, which sets in very rapidly, NO is of great significance for the supply of blood to the organs. Moreover, NO also plays a role as an important messenger substance in other physiological processes. For instance, as a radical trap, NO protects against hypoxia-induced damage and it modulates important components of antioxidative protection. Remarkably, in case of inflammatory processes of the skin, in an interaction with the various cell systems, for example, NO regulates the proliferation and differentiation of skin cells, thus promoting wound healing.

Correspondingly, it has been found in animal models that a reduced NO synthesis rate is associated with a delayed formation of new vessels and with wound healing.

On the basis of these insights pertaining to NO, there are already approaches to use gaseous NO for the therapy of impaired perfusion or chronic wounds. Up until now, NO-containing gas used for therapeutic purposes has been supplied in gas cylinders (industrial gas) so that its storage and handling in a hospital or in another therapeutic institution are demanding in view of the requisite safety measures. This applies especially to a mobile device. Moreover, the quality of the stored gas used for medical applications has to meet strict requirements, and this further increases the demands made in terms of its production and storage. Even a slight contamination of the gas leads to the formation of undesired and conceivably toxic byproducts. Accordingly, European drug and health authorities have laid down strict requirements pertaining to the purity of the nitric oxide to be used. Aside from the use of "technical" NO gases for medical applications, there are methods for the plasma-chemical production of nitric oxide. These methods require subsequent, sometimes very demanding, purification procedures, and it is difficult to set the optimal concentration of NO for the therapeutic objective in question.

Figure 2:
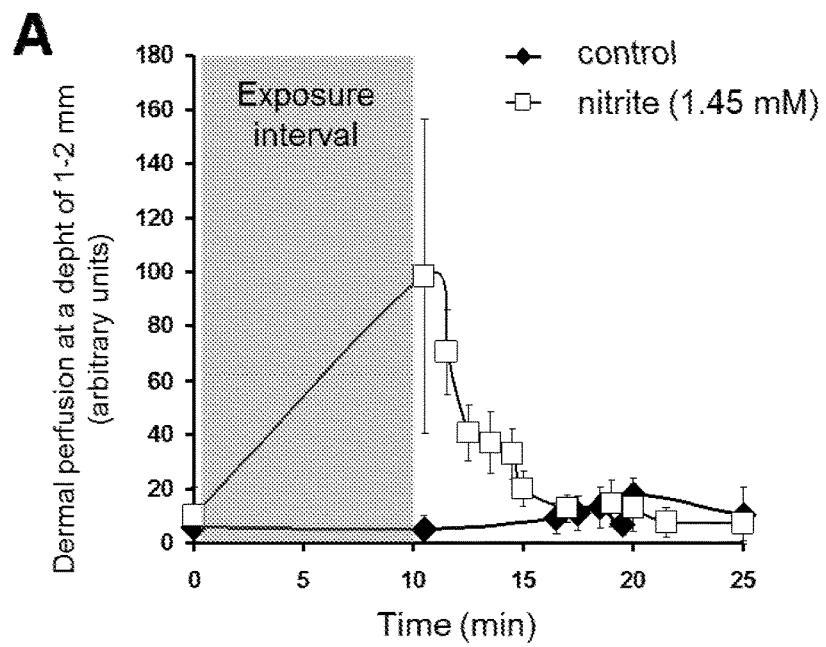
Figure 2:
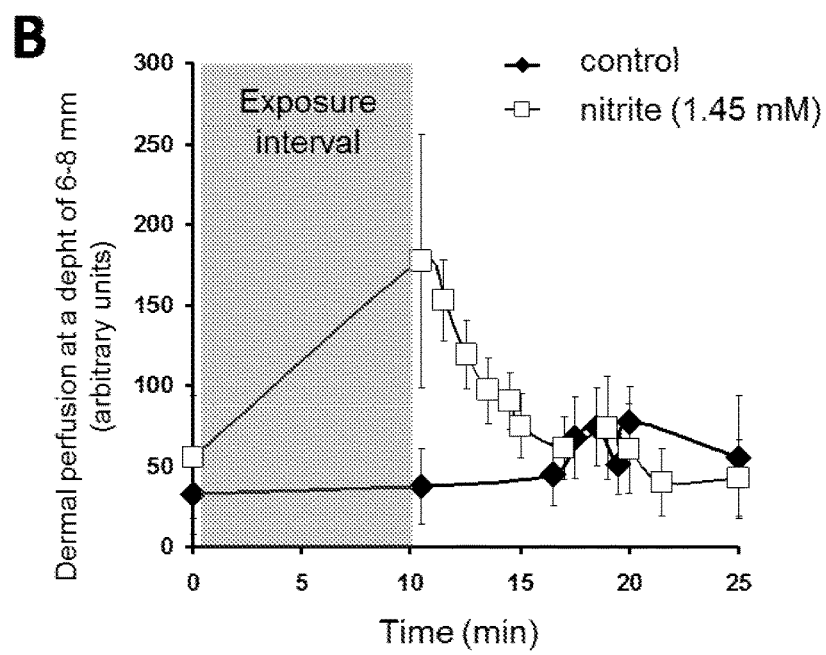

Opländer et al., 2010 (Nitric Oxide Biology & Chemistry, 23: 275-283) describe a method for the continuous formation of high-purity NO gas mixtures through the controlled UVA photolysis of nitrite solutions. In FIG. 2, this document shows two apparatuses that, by means of UVA radiation of a nitrite solution, generate an NO-containing gas mixture that is obtained at the outlet of the apparatuses (indicated with ">CLD"). These units are not configured as immersion devices.

International patent document WO 2002/074223 relates to a foot-massage apparatus and it discloses a removable water vessel 130 which is equipped with a UV lamp 225 installed on the top which is intended to sterilize the water. This document, however, does not provide for any connection between the water vessel and the foot-bath unit. Another drawback of WO 2002/074223 is that it makes no provision for circulation or pumping equipment by means of which the aqueous solution can be conveyed from the water vessel into the foot bath and back again, thus creating a closed circuit between the two compartments.

International patent document WO 2003/003989 A1 discloses a device for healing wounds and for infection control, whereby it discloses a housing 12 into which a foot 100 can be inserted and whereby a UV lamp 14 serves to stimulate the photoactivatable material placed into the housing in order to, among other things, form NO. The NO-containing gas mixture can circulate in the housing thanks to a fan 50. According to WO 2003/003989 A1, there is no separation between the NO-generating unit and the immersion device and the latter is also not suitable to receive an aqueous solution as the carrier medium. Moreover, in WO 2003/003989 A1, the part of the body cannot be treated in a temperature-controlled manner.

U.S. Pat. Appln. No. 2013/096490 discloses a system for healing wounds and, in paragraph [0031], it discloses a foot bath comprising a treatment vessel 800 that has a chamber 810 to receive the part of the body that is to be treated. The chamber can be closed off with a cover that is fitted with LEDs on the inside (see [0011]). In the case of a photolysis of the NO donors, these LEDs, which are intended to provide a illumination, would generate the NO directly in the treatment vessel and thus subject the user to the risk of exposure to gaseous NO.

Consequently, there is still a need for new methods for treating impaired perfusion and chronic wounds.

Before this backdrop, the objective of the invention is to put forward a new therapeutic approach for treating impaired perfusion and chronic wounds which is improved with respect to at least one of the above-mentioned drawbacks.

SUMMARY OF THE INVENTION

According to the invention, this objective is achieved in that an immersion device is provided comprising the following:

a. a nitric oxide (NO)-generating unit in which NO is generated by means of physical-chemical stimuli through cleavage from nitric oxide donors (NOD) that are dissolved in a solvent medium that serves as the carrier medium, and b. a volume unit for purposes of immersing objects and especially parts of the trunk, parts of the body or entire bodies, which is associated with the NO-generating unit and which can hold an immersion medium that serves as the carrier medium and that is enriched with the NO generated in the NO-generating unit.

The immersion device according to the invention combines several decisive advantages in comparison to the therapeutic approaches known from the state of the art.

The separation of the NO-generating unit from the volume unit into which the objects can be immersed goes hand in hand with increased safety. For instance, the nitric oxide donors, which might be detrimental or harmful to health, are retained selectively in the NO-generating unit, without coming into contact with the objects that are to be immersed, and only the NO is transferred via the connection between the NO-generating unit and the volume unit.

In the case of the advantageous method of photochemical NO generation according to the invention, which preferably works by means of UV radiation, the UV source can therefore easily be shielded and the user can be protected against exposure to harmful UV radiation.

Moreover, this separation also allows the control and regulation of the content and purity of the NO-containing carrier medium that is being transferred into the volume unit and, in extreme cases, the connection between these two units can be completely interrupted (for example, by means of a safety valve).

Normally, the short half-life of NO hampers its therapeutic use. Thanks to the device according to the invention, despite the short half-life, a constant NO level can be maintained thanks to a continuous NO after-synthesis.

This capability of regulation and control is a decisive advantage, precisely in the therapeutic realm, since it allows treatment that is tailored to a given patient.

The modular structure also permits the use of NOD refill containers (for example, in the form of cartridges), which can ensure a reproducible and reliable production of NO.

A simple adaptation of the volume unit in terms of size, shape and material makes it possible to implement a wide array of NO-dependent immersion applications, ranging from the effect on products such as equipment and instruments, all the way to the therapeutic treatment of human and animal organisms involving the immersion of parts of the body or the entire body.

Since the NO-generating unit is a component of the immersion device according to the invention, it is possible to dispense with an external supply of NO, which usually involves gas cylinders.

This permits its utilization as a mobile system which, precisely in the therapeutic realm, allows its use outside of doctor's offices and clinics, and therefore translates into a more cost efficient treatment and greater patient compliance, particularly in the case of chronic diseases.

The immersion device according to the invention is a device with a simple design and made with commercially available components, so that it is not only cost effective to produce but also easy to use and it is not prone to errors.

In summary, the immersion device according to the invention constitutes an NO-based therapy modality by means of which inexpensive, reliable and safe mixtures containing NO can be created which are tailored to the patient.

The Invention in Detail

In a second aspect, the invention puts forward an immersion device comprising the following:

a nitric oxide (NO)-generating unit having a source of UV radiation and a volume chamber for the immersion of objects and especially of parts of the trunk, parts of the extremities or entire bodies, whereby the volume chamber can hold a solvent medium that serves as the carrier medium, in which, by means of UV radiation from this source of UV radiation, NO is generated from nitric oxide donors (NOD) by means of cleavage, and the solvent medium that serves as the immersion medium is enriched with the NO.

In a third aspect, the invention puts forward an immersion device that comprises the following units and especially that is made up of the following units:

a. a nitric oxide (NO)-generating unit having a source of UV radiation and a volume chamber to hold a NOD-containing carrier medium, whereby the NO-generating unit is configured in such a way that the carrier medium can be enriched with NO by means of UV radiation, and b. a volume unit for purposes of immersing objects, whereby the volume unit can hold the carrier medium that has been enriched with NO and that was transferred from the NO-generating unit.

In one embodiment, the volume unit of the immersion device according to the invention is a container that is open towards the top. As a result, the volume unit can be easily filled with the immersion medium that serves as the carrier medium, and the object that is to be immersed is dipped from above into the volume unit and thus into the immersion medium.

In a preferred embodiment, the NO-generating unit of the immersion device can be tightly sealed. In this manner, none of the NO from the unit responsible for generating the NO can escape into the environment, but instead, it is selectively transferred into the carrier medium, thus being completely available for the (therapeutic) immersion application. This configuration is particularly advantageous within the scope of therapeutic application since the user is not unnecessarily exposed to NO.

In one embodiment of the invention, the solvent medium of the NO-generating unit is identical to the immersion medium of the volume unit. In this manner, the solvent medium enriched with NO can be conveyed from the NO-generating unit into the volume unit and preferably returned from there to the NO-generating unit once again so that a closed circuit exists for this medium. As a result, the "spent" immersion medium can be "regenerated" in the NO-generating unit by means of circulation and renewed NO enrichment.

In an alternative embodiment of the invention, the solvent medium of the NO-generating unit is not identical to the immersion medium of the volume unit. Since these two compartments are associated with each other, there is a need here for a separating means that is permeable to NO (e.g. a membrane or a diaphragm). In this manner, the composition of both media can be optimally adapted to a given application purpose, in other words, the solvent medium for the NO generation in the NO-generating unit and the immersion medium for the immersion of bodies in the volume unit. Consequently, nitric oxide-generating donors can be employed which, as an ingredient of the bathing solution, would be irritating to the skin or even harmful to health. On the other hand, the immersion medium can be provided with substances or substance mixtures which would otherwise disintegrate under UV radiation or even impair or suppress the generation of NO in the NO-generating unit.

In one embodiment of the immersion device, the NO-generating unit has a volume chamber that communicates with the volume unit, whereby the volume chamber contains a carrier medium which can be conveyed through the volume chamber of the NO-generating unit and back into the volume unit by means of circulation or pumping equipment.

In one embodiment of the invention, the volume chamber of the NO-generating unit as well as the volume unit are associated with each other via one or more openings located in a shared wall or via one or more lines, that is to say, the carrier medium can be transported through the opening(s) or the line(s) from the NO-generating unit to the volume unit and then back again.

A line as set forth in the invention can be any means employed for purposes of transporting the liquid, viscous or gel-like carrier medium according to the invention. Examples of such lines are pipes, hoses or channels that are advantageously integrated into the pumping equipment.

Preferably, the volume chamber of the NO-generating unit and the volume unit are associated with each other via two openings located in a shared wall or else via two lines.

In a practical manner, the volume chamber of the NO-generating unit and the volume unit form a closed circuit for the carrier medium so that, after the "spent" carrier medium of the volume unit has been transported back into the NO-generating unit, it can once again be enriched with NO so that, by means of the return transport into the volume unit, the desired concentration of NO can be re-established. This closed circuit is easiest to ensure by means of the above-mentioned two openings or two lines.

According to the invention, the solvent medium as well as the immersion medium can be considered as the carrier medium.

In one embodiment, the carrier medium is an organic or inorganic, liquid, viscous to gel-like carrier medium.

In a preferred embodiment, this carrier medium is an aqueous solution, and especially preferably, an aqueous buffer solution.

The solvent medium of the NO-generating unit is characterized in that the gaseous, liquid or gel-like carrier medium contains one or more NO donors (NOD).

In a preferred manner, the solvent medium also contains one or more of the following substances: catalysts, detergents, buffering substances, chromophores, substances that stabilize the NOD such as, for example, dimethyl sulfoxide or ethanol, substances that increase the half-life of NO such as those described, for example, in U.S. Pat. Appln. No. 2003/0039697, NOD stabilizers, antioxidants, dyes, pH indicators, care products, fragrances, pharmacologically active substances.

In an especially preferred embodiment, the carrier medium, in other words, the solvent medium and/or the immersion medium, contains a system that breaks down or neutralizes polyoxidized nitrogen oxides, oxygen radical anions, hydroxyl radicals or "hydrated electrons".

In a special embodiment, the system that breaks down or neutralizes polyoxidized nitrogen oxides, oxygen radical anions, hydroxyl radicals or "hydrated electrons" is selected from the group consisting of ascorbic acid, ascorbate, vitamin E, derivatives of vitamin E, thiols, radical traps, enzymes that break down oxygen species or nitrogen species.

When a buffer solution serves as the solvent medium, the pH value is advantageously between 3.0 and 10, preferably between 5.5 and 7.4 and especially preferably between 6.0 and 7.0.

The solvent medium is preferably an isotonic saline solution and especially preferably an isotonic buffered saline solution.

Especially preferably, the aqueous solvent medium has the following composition:
    buffer salts for setting the solution to a pH between 6.0 and 7.4
    50 mM to 250 mM NOD
    50 mM to 250 mM antioxidant In a special manner, the solvent medium has the following composition:
    phosphate-buffered saline solution (PBS) with a pH between 6.0 and 7.4
    100 mM NOD
    150 mM antioxidant
    Preferably, the PBS is a solution having the following composition:
    8 g/l NaCl
    0.2 g/l KCl
    1.424 g/l $Na_2HPO_4$
    0.2 g/l $KH_2PO_4$ In an alternative embodiment, an acetate-buffered saline solution having the following composition is used:
    8 g/l NaCl
    0.2 g/l KCl
    a mixture of acetic acid and sodium acetate with a final concentration ranging from 50 mM to 250 mM The above-mentioned embodiments are also employed in the special case when the solvent medium is identical to the immersion medium.

Preferably, the immersion medium contains one or more of the following substances: catalysts, detergents, buffering substances, chromophores, substances that stabilize the NOD such as, for example, dimethyl sulfoxide or ethanol, substances that increase the half-life of NO such as those described, for example, in U.S. Pat. Appln. No. 2003/0039697, NOD stabilizers, antioxidants, dyes, pH indicators, care products, fragrances, pharmacologically active substances.

Example of substances that increase the half-life of NO are disclosed, for example, in U.S. Pat. Appln. No. 2003/0039697, to whose disclosure reference is hereby made and which is included in its entirety in the present application.

On the basis of the general technical expertise of the person skilled in the art, he/she will select suitable substances or substance mixtures with an eye towards the envisaged application. In this context, he/she will especially take into consideration the fact that physiologically compatible and/or dermatologically compatible safe substances and substance mixtures will be employed when the invention is used as a bathing device.

Preferably, the immersion medium is in the form of a buffer aqueous solution.

When a buffer solution is used as the immersion medium, the pH value is advantageously between 3.0 and 10, preferably between 5.5 and 7.4 and especially preferably between 6.0 and 7.0.

The immersion medium is preferably an isotonic saline solution and especially preferably an isotonic buffered saline solution.

Especially preferably, the aqueous immersion medium has the following composition:
    buffer salts for setting the solution to a pH between 5.0 and 8.0
    100 mM to 250 mM NOD
    100 mM to 250 mM antioxidant In an especially preferred manner, the aqueous immersion medium has the following composition:
    buffer salts for setting the solution to a pH between 6.0 and 7.4
    50 mM to 250 mM NOD
    50 mM to 250 mM antioxidant In a special manner, the immersion medium has the following composition:
    phosphate-buffered saline solution (PBS) with a pH between 6.0 and 7.4

100 mM NOD 150 mM antioxidant

Preferably, the PBS is a solution having the following composition:

8 g/l NaCl 0.2 g/l KCl 1.424 g/l $Na_2HPO_4$ 0.2 g/l $KH_2PO_4$

In an alternative embodiment, an acetate-buffered saline solution having the following composition is used:

8 g/l NaCl 0.2 g/l KCl a mixture of acetic acid and sodium acetate with a final concentration ranging from 50 mM to 250 mM In one embodiment of the invention, the immersion medium contains one or more pharmacologically active substances. These substances can support the pharmacological effect of the NO or else can have a therapeutically relevant effect on a given disease, independently of the NO.

In one embodiment of the invention, the immersion medium contains one or more of the following pharmacologically active substances: anti-inflammatory agents such as, for instance, nonsteroidal anti-inflammatory drugs (NSAIDs) or corticoids, immunosuppressants, antibiotics, anticoagulants, antithrombotic agents, antiviral agents, antimycotic agents, local aesthetics and analgesics.

However, within the scope of a combined treatment, these additional pharmacologically active substances can also be not only a constituent of the immersion medium but they can also be used before or after the bathing procedure.

In one embodiment of the invention, the immersion device creates an effervescent bath. This can be achieved by blowing in a gas or by a chemical reaction in which a gas-forming substance such as, for example, carbonate salt is induced to release $CO_2$ gas by acidifying the solution.

In another embodiment of the invention, the immersion device is provided with a means that reduces or completely prevents the release of NO into the environment. This can be a physical separation, for example, in the form of a hood or cover film that covers the volume unit, whereby it has a cutout for the part of the body that is to be immersed. As an alternative, this can be an exhaust system which draws off the NO released from the immersion medium and then feeds it either into the immersion medium or into the solvent medium, or else breaks down or filters off the NO.

In a preferred embodiment, the NO-generating unit is an essentially closed system, that is to say, a system that is hermetically sealed vis-à-vis the environment and that is only in communication with the volume unit. This ensures that the NO generated in the NO-generating unit is (preferably selectively) transferred to the volume unit and cannot escape into the environment.

In another embodiment, the NO-generating unit is coupled to an NO sensor so that the amount of NO generated can be flexibly adapted as feedback to the measured NO value.

This NO sensor, which serves as a measuring apparatus to quantify the NO, can be installed in the NO-generating unit, in the volume unit or else on the outside of the immersion device. In a special embodiment, the control unit associated with the NO sensor ensures that the NO-generating unit completely halts the generation of NO whenever a critical NO value is exceeded.

In one embodiment of the invention, the NO-generating unit is actuated in such a way that the content of NO in the immersion medium is kept constant over the period of time of the treatment.

In an alternative embodiment of the invention, the NO-generating unit is actuated in such a way that the content of NO increases or decreases over the period of time of the treatment.

In another embodiment of the invention, the immersion device is employed to treat objects, equipment or instruments. The effect that NO has on these objects makes it possible to clean or disinfect them, to reduce the microbial load or to diminish or remove a biofilm.

In a preferred embodiment, the immersion device is used to clean or disinfect medical or surgical instruments.

In one embodiment of the invention, the NO is generated by a plasma-chemical modality. Aside from the use of "technical" NO gases for medical applications, there are methods for the plasma-chemical production of nitric oxide. International patent application WO 95/07610 A, U.S. Pat. No. 5,396,882 A and German patent application DE 198 23 748 A are publications that disclose methods for the plasma-chemical production of NO in which NO is produced under the effect of a glow discharge, spark discharge or arc discharge in a processing gas containing nitrogen ($N_2$) and oxygen ($O_2$). When a gas discharge of the described type is carried out at excessively low temperatures (as is observed in case of a glow discharge), it results in a low efficiency of the NO production in a gas mixture. Moreover, primarily the $NO_2$ radical ($NO_2^-$), which is undesired for inhalation purposes, is generated under these conditions. In order to remove the $NO_2$ radical from the inhalation gas, it is necessary to employ complex absorber technology. The drawback of an absorber is especially the fact that the absorber material has to be frequently replaced or regenerated. A spark discharge or an arc discharge, both of which have higher energy than a glow discharge, brings about a relatively pronounced heating of the gas, resulting in a commensurately efficient production of NO. The high thermal load exerted on the electrodes, especially at the point of contact of the spark, however, disadvantageously causes severe electrode erosion, that is to say, progressive disintegration of the electrode material. Due to this electrode erosion, the method is, on the one hand, maintenance-intensive because the electrodes are highly prone to wear. On the other hand, it has to be prevented that patients are exposed to the eroded electrode material that has been finely dispersed in the gas. This necessitates a labor-intensive purification of the gas.

NO can also be generated by means of the electrolytic and thermolytic cleavage of appropriately labile NO derivatives (NO donors).

NO can also be produced by means of photolysis. According to this method, for instance, the nitrite ions ($NO_2^-$) present in a solution containing nitrite (e.g. sodium nitrite) are cleaved (photolysis) by means of electromagnetic radiation (e.g. UVA radiation at wavelengths between 320 nm and 440 nm), as a result of which NO is generated. Under reductive conditions or in an inert gas atmosphere (e.g. nitrogen), the decomposition of nitrite induced by the electromagnetic radiation takes place via different channels, some of which are also parallel but weighted differently thermodynamically. It can be assumed that in channel 1 (Reactions 1 to 5), UVA radiation (with an optimum at 354 nm to 366 nm) cleaves nitrite to form the nitric oxide radical (NO.) and the oxygen radical anion (O.$^-$) (Equation 1). The latter product subsequently initiates the formation of the reactive hydroxyl radical (OH.) (Equation 2) in aqueous solutions. The hydroxyl radical reacts with nitrite, leading to the formation of the nitrogen dioxide radical ($NO_2$.) (Equation 3). This can then further react with nitric oxide to form dinitrogen trioxide ($N_2O_3$) (Equation 4).

$$NO_2^- + h\nu \rightarrow N. + O.^- \qquad (1)$$

$$O.^- + H_2O \rightarrow OH. + OH^- \qquad (2)$$

$$NO_2^- + OH. \rightarrow NO_2. + OH^- \qquad (3)$$

$$NO_2. + NO. \rightarrow N_2O_3 \qquad (4)$$

$$N_2O_3 + H_2O \rightarrow 2NO_2^- + 2H^+ \qquad (5)$$

It seems that, in channel 2 (Equations 6 to 10), hydroxyl radicals do not play any role under the conditions cited, although a "hydrated" electron ($e^-_{hyd}$) as well as a nitrogen dioxide radical are formed (Equation 6). In the presence of an excess of nitrite, the electron is transferred to the nitrite, and the resultant nitrite anion (Equation 7) is reduced in water to form the NO radical (Equation 8). The following reactions in Equations (9) and (10) correspond to those in Equations (4) and (5). In this process, the weighting of channel 1 to channel 2 forms a ratio of about 40:60.

$$NO_2^- + h\nu \rightarrow NO_2. + e^-_{hyd} \qquad (6)$$

$$e^-_{hyd} + NO_2^- \rightarrow NO_2^{2-} \qquad (7)$$

$$NO_2^{2-} + H_2O \rightarrow NO. + 2OH^- \qquad (8)$$

$$NO. + NO_2^- \rightarrow N_2O_3 \qquad (9)$$

$$N_2O_3 + H_2O \rightarrow 2NO_2^- + 2H^+ \qquad (10)$$

As can be seen from Reactions 1 to 10, the photolytic decomposition of nitrite is accompanied by a parallel production of reactive and cytotoxic chemical species. Moreover, from the reactions in Equations (4) and (9), it can also be seen that $NO_2$ radicals ($NO_2.$) can undergo a backward reaction with the NO formed in Equation (1).

It has been recognized (European patent application EP 1903003 A1) that, through the use of at least one system that breaks down or neutralizes $NO_2$ radicals or oxygen species during the generation of nitric oxide, the formation of the above-mentioned reactive intermediate products of light-induced nitrite decomposition ($NO_2^-$, $O.^-$, $OH^-$, $e^-_{hyd}$) is suppressed or else they are eliminated, while, at the same time, there is no reduction in the generation of nitric oxide. Therefore, the yield of freely available NO and the purity of the gas are enhanced.

The increase in the release of NO as well as the high degree of purity stem from a reaction-induced elimination of the reactive intermediate products, for instance, according to the following Reactions (11) to (17).

$$N_2O_3 + RS^- \rightarrow NO_2^- + RSNO \qquad (11)$$

$$RSNO + h\nu \rightarrow NO. + RS. \qquad (12)$$

$$NO_2. + RS^- \rightarrow NO_2^- + RS. \qquad (13)$$

$$NO. + RS \rightarrow RSNO \qquad (14)$$

$$BA + OH. \rightarrow BA\text{-}OH \qquad (15)$$

$$VitC + NO_2. \rightarrow NO_2^- + VitC.^- \qquad (16)$$

$$Trol + NO_2. \rightarrow NO_2^- + Trol.^- \qquad (17)$$

(Abbreviations: $RS^-$=thiol; RSNO=S-nitrosothiol; RS.=thioyl radical; BA=benzoic acid; VitC=vitamin C, ascorbate, ascorbic acid; VitC.=the radical of VitC; Trot=trolox; Trol.=the radical of trolox)

Thanks to the presence of these and other functionally equivalent systems during the formation of nitric oxide, this method (European patent application EP 1903003 A1) accounts for a high yield of nitric oxide while, at the same time, the formation of undesired (poly)oxidized nitrogen oxides, especially $NO_2$. as well as of hydroxyl radicals and reactive hydrated electrons is effectively prevented, or else these substances are eliminated after having been formed, or else they can only be produced in such small quantities that they remain in solution and cannot change over to the gas phase. Therefore, these substances cannot cause, for example, any pathologically relevant damage due to inhalation of the inhalation gases.

Substances (antioxidants) that break down or neutralize reactive nitrogen species (ROS) or nitrogen oxide species (RNS) are preferably used as the systems that break down or neutralize reactive nitrogen oxide species (e.g. nitrogen dioxide radicals) or reactive oxygen species. It is likewise preferred for these to be ascorbic acid, ascorbate, vitamin E and its derivatives, thiols, other antioxidants, radical traps or enzymes that break down ROS and RNS.

The person skilled in the art is familiar with numerous antioxidants that he/she will select for NO generation as a function of the carrier medium and of the mechanism in question.

Examples of a suitable lipophilic carrier medium that can be provided by means of an organic solvent are antioxidants such as tocopherols, tocotrienols, tocomonoenols, butylated hydroxyanisole (BHA) and butylated hydroxytoluene (BHT).

Particularly well-suited for a hydrophilic carrier medium, here especially preferably aqueous solutions, are organic sulfurous compounds such as glutathione, cysteine or thiolactic acid or also organic acids such as ascorbic acid, α-lipoic acid, hydroxycinnamic acids such as p-coumaric acid, ferulic acid, sinapinic acid or caffeic acid, or else hydroxybenzoic acids such as gallic acid, protocatechuic acid, syringic acid or vanillic acid.

Other preferred antioxidants comprise polyphenolic compounds such as anthocyanins, flavonoids and phytoestrogens.

Moreover, it has been found that the binding or elimination of the above-mentioned reactive intermediate products of light-induced nitrite decomposition ($NO_2^-$, $O.^-$, $OH^-$, $e^-_{hyd}$) can also take place in the neutral pH range, whereby a maximum NO release with a maximum level of purity can be obtained from nitrite.

Acidic conditions (pH<7.0) are conducive to "spontaneous" nitrite decomposition in aqueous solutions. In accordance with Equations 18 to 20, the nitrite anion ($NO_2^-$) in aqueous solutions is in a state of equilibrium with its conjugated acid, namely, nitrous acid ($HNO_2$). $HNO_2$, in turn, is in a state of equilibrium with dinitrogen trioxide ($N_2O_3$), which spontaneously decomposes to form NO. and $NO_2.$.

$$NO_2. + H^+ \leftrightharpoons HNO_2 \qquad (18)$$

$$2HNO_2 \leftrightharpoons N_2O_3 + H_2O \qquad (19)$$

$$N_2O_3 \leftrightharpoons NO. + NO_2. \qquad (20)$$

Therefore, in one embodiment of a described method (European patent application EP 1903003 A1), the UVA-induced generation of nitric oxide preferably takes place within a pH range from 0 to 12, particularly from 1 to 10, particularly preferred from 1.5 to 6, especially from 2 to 6 and very especially from 2.5 to 4.

The content of NO in the solvent medium and/or immersion medium is between 10 μM and 5 mM, preferably between 50 μM and 2 mM, and especially preferably between 100 μM and 200 μM.

Depending on the nitrite or antioxidant concentration employed as well as on the magnitude of the physical decompensation stimulus used that leads to the decomposition of the nitrite, a high concentration of nitric oxide can be obtained by means of the cited method (European patent application EP 1903003 A1).

In a solution, the quantity of generated nitric oxide can be controlled by means of the employed concentration of the agents that release nitric oxide and by means of the physical and/or chemical induction that is responsible for the release of nitric oxide from the agents.

In this context, the expression "physical and/or chemical induction" refers not only to the intensity of the electromagnetic radiation but also to the duration of the exposure to which the reaction solution is subjected; it also generally refers to the reaction parameters that have an influence on the formation of nitric oxide itself as well as on the concentration of nitric oxide. Generally speaking, these parameters include the pH value of the reaction solution, the redox status of the reaction solution, the temperature of the reaction solution, the surface area exposed to radiation, the duration of action of an induction quantity on the agents that release nitric oxide, the distance between the source of electromagnetic radiation and the reaction solution, the spectrum of the source of electromagnetic radiation, the absorption, transmission and reflection properties of the reaction solution, the concentration of biological or chemical catalysts or mediators which, even outside of the "typical" physical-chemical conditions needed for an optimal NO release, nevertheless allow NO to be released from NO-generating substances through catalysis or through appropriate acceptor properties. In particular, this expression refers to chromophores and other substances by means of which, for example, electromagnetic radiation outside of the UVA spectrum could also be capable of allowing NO to be released from the appropriate NO-forming agents.

Thus, for instance, at induction quantities that are kept constant, the use of varying concentrations of the substance(s) that release nitric oxide makes it possible to release varying amounts of nitric oxide.

Moreover, at a constant concentration of the substance(s) that release nitric oxide, the release of nitric oxide can be changed by varying the setting parameters of the appertaining induction quantities. Therefore, at an induction quantity that is kept constant, the use of high concentrations of the NO-releasing substances makes it possible to release large amounts of NO and vice versa. At a constant concentration of the NO-releasing substance, the generation of NO can be changed by varying the setting parameters of the appertaining induction quantities. In this context, the setting parameters can be employed alternatively to or simultaneously with the regulation of the NO generation. Particularly by means of the simultaneous regulation of the NO generation on the basis of several setting parameters, the method can be advantageously optimized in terms of the NO generation as well as in terms of the generation of undesired byproducts.

The substance that is employed for the release of nitric oxide as well as in the method according to the invention is fundamentally not subject to any restrictions, provided that it can release nitric oxide under the effect of electromagnetic radiation. For instance, it can be selected from among the group consisting of:

(a) pure substances or substance mixtures that generate nitric oxide under the effect of electromagnetic radiation;
(b) substance mixtures that, in addition to the substances or substance mixtures cited in (a), also contain auxiliary substances that are selected from the group consisting of photoacceptors, photoamplifiers, transition metals, particularly copper ions, enzymes or catalysts, for purposes of generating nitric oxide either spontaneously or under physical or chemical influences; and
(c) substances or substance mixtures that, only after a preceding chemical reaction employing the substances cited in (a) and, if applicable, the auxiliary substances cited in (b), generate nitric oxide either spontaneously or under physical or chemical influences when exposed to electromagnetic radiation.

Moreover, the substances described in (a) can additionally release nitric oxide due to temperature changes and/or changes in moisture and/or changes in the pH of their solutions and/or changes in the redox status of their solutions.

In a preferred embodiment of the invention, the nitric oxide donors (NOD) are selected from the group comprising organic nitrates, inorganic nitrates, nitrites, sulfur-nitroso, nitrogen-nitroso or oxygen-nitroso compounds, NO-metal compounds and NO-chelating substances.

Nitric oxide donors are known from the state of the art and are familiar to the person skilled in the art. Examples of NOD include diazeniumdiolates (e.g. U.S. Pat. Nos. 7,105, 502; 7,122,529; 6,673,338), trans[RuCl([15]aneN$_4$)NO]$^{+2}$, nitrosyl ligands, 6-nitrobenzo[a]pyrrole, S-nitrosoglutathione, S-nitrosothiol, nitroaniline derivatives (see U.S. Pat. Appln. 2013/0224083), 2-methyl-2-nitrosopropane, imidazoyl derivatives, hydroxylnitrosamine, hydroxylamine and hydroxyurea.

In one embodiment of the invention, the immersion medium and/or the solvent medium are utilized employing a refill container. Here, the ready-to-use formulated medium can be employed by fitting the container into the immersion device and, thanks to the formulation that is defined during the production process, it is ensured that a therapeutically optimal formulation is obtained.

In another embodiment, the ingredients of the immersion medium and/or of the solvent medium are added to the medium in preferably pre-portioned form (so-called packaged unit). Since the NO generation according to the invention is also possible using regular tap water, the user can therefore use tap water and can mix it with the ingredients which comprise, for example, a buffering substance, salts, NOD and antioxidant, thus creating a ready-to-use solvent medium or immersion medium.

The pre-portioned form preferably contains the ingredients in solid form. For instance, they can be present as powder, pulverulent substances, granules, tablets, film tabs, dragées, soft-gel capsules, hard-gel capsules, lozenges, caplets, effervescent tablets or pills, whereby each packaged unit advantageously contains the amount sufficient for one specific treatment.

In a preferred embodiment, the ingredients are present as effervescent tablets. In this form, they dissolve very quickly and also enrich the medium with the appropriate—preferably inert—gas (e.g. $CO_2$). Moreover, this form of administration is well known to users in the realm of bathing applications, as a result of which it translates into a high level of compliance.

As an alternative, the ingredients can be present in liquid or semi-solid form. Semi-solid forms include, for example, suspensions, emulsions, pastes, creams, ointments, gels or lotions. The pre-portioning in the form of a packaged unit can be achieved, for instance, by means of packaging in ampoules, bottles, pouches or tubes.

In another preferred embodiment, the packaged unit is configured in such a way that its form allows error-free use in the immersion device. For instance, the form is preferably that of a cartridge that can only be attached to the immersion device in a specific orientation. Moreover, this cartridge can be equipped with a blocking mechanism that only releases the ingredients in the desired manner after the cartridge has been properly locked in the immersion device. Advantageously, the immersion device here can be equipped with a sensor which detects any incorrect orientation or locking of the cartridge and indicates this to the user.

In another aspect, the invention puts forward a kit comprising a packaged unit for one treatment, whereby this packaged unit contains a pulverulent, gel-like or liquid composition containing a NOD, a buffering substance, an antioxidant and optionally a solvent.

The NO can be released from aqueous nitrite or S-nitrosothiol solutions. In this context, for practical reasons, preference is given to the use of an aqueous solution of sodium nitrite or S-nitrosothiols as the source of NO. The aqueous solution can have a concentration of NO donors preferably amounting to 0.001 mM to 10,000 mM, especially 0.2 mM to 6000 mM, particularly preferably 0.3 mM to 5000 mM, especially 0.4 mM to 2000 mM, very specially 0.5 mM to 1500 mM.

In another embodiment, the aqueous solution that serves as the immersion medium and/or solvent medium has a concentration of the NO donors between 1 μM and 5000 mM, preferably between 100 μM and 2000 mM, particularly preferred between 500 μm and 500 mM and very especially between 1 mM and 150 mM.

The type of radiation from the NO-generating initial substrates is familiar to the person skilled in the art in this field. Any electromagnetic radiation can be employed that is capable of breaking down photolabile NO derivatives while forming nitric oxide. For example, within the scope of the present invention, nitric oxide can be produced by means of photolytic cleavage using UVA radiation at wavelengths of, for example, 320 nm to 440 nm. However, it is likewise possible to employ electromagnetic radiation of any other wavelength which, either on its own or in conjunction with chemical, physical or biological methods, induces a direct photolytic cleavage of NO-generating donors (NO derivatives) that is induced or facilitated or catalyzed by other auxiliary substances.

The production of nitric oxide can also take place in solutions that are saturated with inert gases. In such solutions saturated with inert gases (nitrogen ($N_2$), helium ($H_2$), argon, etc.), the NO that is dissolved therein has a considerably longer useful life and can also remain in solution at higher concentrations. It is generally assumed that the maximum solubility of NO in aqueous solutions is approximately 2 mM. In this context, culture media or infusion media or infusion buffers, serum, blood, gels and all other substances that are capable of picking up gases can also be considered as aqueous solutions.

The nitric oxide produced by means of the photolysis of photolabile NO donors can be used, for instance, for inhalation purposes. Other specific areas of application are the stimulation of the metabolism of tissues through external application, the structural modification of organic as well as inorganic surfaces, sterilization or the creation of cytotoxicity. The nitric oxide generated by means of photolysis can also be used to apply gas to wounds, especially in order to heal chronic, non-healing, possibly bacteria-infested wounds. If the nitric oxide has been generated in saturated liquids, it can also be employed systemically for the treatment of hypertension. Finally, the nitric oxide can also be generated in carriers which are nitrosated with nitric oxide and which spontaneously release NO once again. The nitric oxide can also be employed for the production of a wide array of substances that bind NO (e.g. NO donors).

The quality of a gas that has been stored in or introduced into solutions and that is intended for medical applications has to meet stringent requirements. Even a slight contamination of the gas leads to the formation of undesired and conceivably toxic byproducts. The formation of these byproducts during prolonged storage of gas cylinders containing nitric oxide as well as during the production of nitric oxide using a plasma technique and also the removal of these radicals constitute a major technical as well as financial drawback. The advantages of the photolytic method for the production of solutions containing nitric oxide are the simplicity of the methods for the production of the gas containing NO, the particularly high degree of purity of the NO gas mixture produced, the low follow-up costs and the absence of storage costs, the very simple handling of the NO production as well as the purity control, and the incomparably favorable ratio of the production costs to the amount of NO gas produced.

Device According to the Invention

For external application, NO can be used in the form of a gas or plasma containing NO as well as in the form of an NO donor that breaks down either spontaneously or through induction. The present invention relates to a medical bathing device that can use physical-chemical stimuli to cleave nitric oxide donors that are dissolved in a solvent medium, for example, in a bathing solution, and to enrich the solvent medium, for example, the bathing solution, with the nitric oxide thus produced, so that the device and the bathing solution can be used to enhance medical therapies in humans and animals as well as to enrich various media with NO.

In one embodiment of the invention, the immersion device is employed for the treatment of diseases. In this context, preferably parts of the trunk, parts of the body or entire bodies are immersed into the immersion medium containing NO.

Therefore, the immersion device according to the invention can be used not only to treat chronic or acute diseases but also conceivably to prevent such diseases. Unless otherwise indicated, the terms "therapy" or "treatment" encompass all measures aimed at ameliorating, healing or preventing the diseases in question here.

The above-mentioned physical stimuli for the cleavage of NO donors can be the pH value, electrical current, heat or electromagnetic radiation, in other words, stimuli that are capable of cleaving pH-labile, electrolabile, thermolabile or photolabile NO donors in a pH-dependent, electrolytic, thermolytic or photolytic manner while concurrently releasing NO.

Due to the limited dissolving behavior of NO, it is possible to generate in appropriate solutions NO concentrations that are physiologically relevant but that are far below those that could be harmful to the health of humans. Moreover, a direct contact of the surface of the human body with the solutions containing NO translates into a considerably more accurate NO treatment than, for instance, with gas mixtures containing NO or with spontaneously disintegrating NO donors. Moreover, the fact that, depending on the level of the load with the appertaining NO donor, the device can be used by different end consumers—ranging from laypersons all the way to professionals—constitutes an essential advantage of the device according to the invention in comparison to other NO-based therapies.

The device according to the invention consists of a volume-holding container (hereinafter referred to as volume unit) that can hold the solvent medium or media solutions, for example, bathing solutions, and it also consists of another technical unit (hereinafter referred to as nitric oxide-generating unit) that can generate nitric oxide in the solvent medium and can thus enrich the solvent medium of the volume unit with NO.

However, there is also the possibility that the NO-generating unit does not generate the NO directly in the solvent medium of the volume unit, but rather, in a different solution, which is then mixed with the solvent medium of the volume unit at the desired degree of dilution. As an alternative, even an NO-containing gas mixture generated in the NO-generating unit or an NO-containing gas mixture obtained from a gas cylinder can be introduced into the solvent medium of the volume unit so that the solvent medium of the volume unit, for instance, a bathing solution, can be enriched with NO.

Parts of the body can be immersed into and bathed in such a bathing solution enriched with NO for therapeutic purposes. These can be parts of the trunk or of the extremities of humans and animals. Since, depending on the envisaged application, the volume unit can have a volume ranging from 0.001 liter to 1000 liters and more, small parts of the trunk and of the extremities can be treated and even entire bodies can be immersed, whereby such a treatment can last between a few seconds and many hours.

In one preferred embodiment of the invention, the body or the part of the body that is to be treated is immersed into the immersion medium for 5 to 30 minutes, preferably between 7.5 to 20 minutes and especially preferably for 10 to 15 minutes.

In a preferred manner, such a bath is employed several times daily, whereby preference is given to its use 2 to 3 times per day.

For purposes of controlling the duration of the treatment, there is preferably a time-control unit which switches off the generation of NO after a prescribed fixed, or preferably flexibly programmable, period of time.

Moreover, the immersion medium can contain a dye whose color changes after a given period of time, so that the user is thereby informed about the end of the treatment.

Moreover, the immersion device can also comprise a device for measuring the perfusion, which, on the basis of the therapy outcome, permits an excellent control of the duration and/or intensity of the treatment. The person skilled in the art is familiar with numerous devices for measuring perfusion. Examples of this are vascular tachometers or the microsensor disclosed in international patent document WO 97/46853. This sensor comprises an indicator-permeable insert that is arranged in an opening of an indicator container which is formed by a vessel, so that the insert forms a permeable wall section of the container.

Other vascular-related measuring parameters such as reddening of the skin or the skin temperature can serve as surrogate parameters for the perfusion of the skin; appropriate measuring methods and equipment for these parameters are known from the state of the art.

The NO-generating unit generates the nitric oxide in order to enrich, for example, bathing solutions by means of pH-induced electrolytic, thermolytic or any other physically induced cleavage, preferably, however, by means of the photolytic cleavage of nitric oxide donors. In this context, the NO-generating unit can be an integral component of the entire device and it can be permanently joined to the volume unit. Alternatively, the NO-generating unit can also be an autonomous, external unit that is not installed on the volume unit.

An essential characteristic of the NO-generating unit, however, is that it likewise has its own volume, which is connected to the volume of the volume unit, and that the volume of the NO-generating unit, with all of its conceivable contents, can be subjected to the appropriate physical stimulus in order to generate NO from chemical NO donors. Alternatively, however, the NO-generating unit can also be employed to generate gas mixtures that contain NO and that are fed in from the outside in order to produce solutions that are enriched with NO, for instance, bathing solutions.

Below, by way of an example, in conjunction with a special embodiment of the device according to the invention, electromagnetic radiation is discussed as the relevant physical stimulus for the cleavage of chemical NO donors.

Electromagnetic radiation can be emitted by a light source that can be installed inside and/or outside of the nitric oxide-generating unit. It is important for the flooding of light through the contents of the NO-generating unit, together with the reaction substances that release nitric oxide, to be at a maximum with an eye towards an induced breakdown of the substance or a release of nitric oxide. The source of the electromagnetic radiation here can be a glow-discharge or gas-discharge lamp (low-pressure discharging or high-pressure discharging source) coated with appropriate fluorochromes, light-emitting diodes (LED), organic light-emitting diodes (OLED), lasers, or any other source of electromagnetic radiation that is capable of generating NO from the appertaining chemical donors or substrates.

For purposes of attaining optimal cleavage of the photolabile NO donors dissolved in the bathing solution, the light source that irradiates the volume of the NO-generating unit can emit electromagnetic radiation at wavelengths of 100 nm to 2000 nm or else electromagnetic radiation of any other wavelength that, either on its own or in conjunction with chemical, physical or biological methods, can induce the cleavage of nitric oxide donors and thus the release of nitric oxide.

For this reason, the NO-generating unit should preferably be made of a material which does not influence the properties of the energy of a source of electromagnetic radiation that is needed for an optimal release of nitric oxide, or else which, owing to its properties, first creates or optimizes the light properties needed for a light-induced release of nitric oxide, or which, in case of the pH-dependent NO generation, promotes and optimizes the pH-induced nitrite decomposition.

According to the invention, the NO-generating unit comprises a volume chamber that holds the carrier medium with nitric oxide donors (NOD) and also a device for generating NO from the at least one NOD.

This can be a device for adding acid to the volume chamber, where the NO is then generated in a pH-induced manner.

In a preferred embodiment, the NO-generating unit is provided with a source of UV radiation whose UV radiation generates the NO directly in the carrier medium by means of photolytic decomposition. This entails the advantage that the carrier medium can be present in a sealed-off compartment, in addition to which the NO generation can take place in a controlled and reproducible manner.

For purposes of the generation of the NO, the carrier medium in the NO-generating unit is preferably irradiated by the source of radiation in a flat container.

For instance, a container having a layer thickness of between 1 mm and 20 mm, preferably between 2.5 mm and 10 mm and especially preferred between 5 mm and 7.8, is suitable for the photolytic cleavage. It has been shown that a layer thickness that is appropriately dimensioned translates into a high yield of NO due to the optimal utilization of the UV radiation.

Advantageously, the material for the container is permeable to UV radiation. On the basis of his/her knowledge, the person skilled in the art can choose the suitable materials for the container that holds the carrier medium. In the case of UV radiation in the UVA range (315 nm to 380 nm), conventional soda-lime glass can be used, whereas, in the case of higher-energy radiation of up to 290 nm, borosilicate glass can be employed, while in the case of UV radiation below 290 nm, quartz glass is well-suited.

Ultraviolet-permeable plastics such as polymethyl pentene (PMP), modified polymethyl methacrylate (PMMA) and modified polyvinyl butyral (Trovisol UV+®) can be used as the material for the container.

In a preferred manner, the container is shaped in such a way that its surface facing the source of radiation is at a defined, constant distance. When it comes to a tubular source of radiation, the container is correspondingly shaped like a hollow cylinder in whose center the electron tube is positioned. Here, the carrier medium is advantageously fed in at one end of the cylinder, it flows along the entire length of the cylinder past the source of UV radiation, a process in which it is increasingly enriched with NO, and it then leaves the cylinder at the other end in order to be fed into the volume unit.

As an alternative, the container can also be a tube that is shaped like a spiral with a defined inner diameter, whereby the tubular UV source is arranged in the center of the spiral. This arrangement allows a gradual rise in the NO concentration, whereby the NO yield can be regulated here by the flow rate in the spiral, while the radiation intensity remains constant.

In an alternative embodiment, in the case of a flat source of radiation (e.g. by means of an LED panel), the container is shaped like a flat box. This box preferably has diametrically installed inlets and outlets for the carrier medium and its interior can also have dividers that can regulate the flow of the carrier medium in a suitable manner.

In another embodiment, the container is provided with a UV-reflective coating on the side facing away from the radiation source. In this manner, the radiation yield can be additionally increased in that the reflected UV light can once again pass through the carrier medium, photolytically generating NO in this process. The person skilled in the art is familiar with appropriate UV-reflecting layers such as, for instance, aluminum or dielectric layers. In an alternative embodiment, the UV-reflecting coating is not applied to the container itself, but instead it is applied separately, for example, to the inner wall of the NO-generating unit.

In one embodiment, the photolytic NO generation is carried out prior to the treatment, as a preliminary step, in order to build up the therapeutically required NO concentration within a time span of 30 minutes at the maximum, preferably between 10 and 15 minutes, especially preferred in less than 10 minutes.

In order for the bathing solution held in the volume unit to be enriched with NO, the bathing solutions of the volume unit can be passed through the volume of the NO-generating unit, then exposed there to the electromagnetic radiation emitted by the light source of the NO-generating unit, and then once again conveyed into the volume unit of the device that holds the main volume. This volume movement that takes place between the volume unit and the NO-generating unit is carried out by pumping equipment, whereby the circulation equipment can be an integral part of the NO-generating unit or of the volume unit, or else it can function completely as an external part of the device.

The person skilled in the art is familiar with pumping or circulation equipment from the state of the art and can select the appropriate apparatus on the basis of the relevant parameters such as the viscosity of the carrier medium, the requisite pump output, the volume of the volume unit and the volume of the NO-generating unit.

The following are examples of pumping equipment: peristaltic pumps, diaphragm pumps, piston pumps, magnetic coupled pumps and impeller pumps.

The immersion device is suitably provided with a temperature-control unit. This allows a selected temperature to be set by means of heating and/or cooling. The temperature is one of the parameters that determine the NO yield and the solubility of the generated NO. Moreover, in this manner, a bath temperature that is optimal for the therapeutic treatment can be set for the bathing application. This can be a temperature between 23° C. and 28° C. [73.4° F. and 82.4° F.] that is comfortable for the user, or else a temperature between 5° C. and 15° C. [41° F. and 59° F.], which thus increases the perfusion of the skin.

Temperature-control units are known to the person skilled in the art and he/she can select the appropriate unit on the basis of the relevant parameters such as the volume of the liquid and the heating and cooling rates.

In a preferred embodiment, the temperature-control unit is necessary, especially in conjunction with a source of (UV) radiation, since the latter causes the carrier medium to heat up. In order to counter overheating of the medium, cooling has to be undertaken in the case of prolonged or intense radiation.

In another embodiment, the source of electromagnetic radiation is employed not only within the scope of the NO generation but also as the heat source of a temperature-control unit.

As the central component of the device according to the invention, the NO-generating unit is either an open system or else it is tightly sealed. The NO-generating unit is characterized in that it is physically joined to the entire device, or else it is loosely connected to it and can be easily exchanged so that it is only placed into the entire apparatus shortly before the device is going to be used.

Another characteristic of the NO-generating unit of the device according to the invention is that replaceable or exchangeable volume-holding filling containers (for example, replacement containers, inserts, cartridges, pads, etc.—hereinafter referred to as filling containers) can be inserted into an NO-generating unit, whereby these containers can preferably release chemically stable or stabilized, potentially NO-storing and thus potentially NO-releasing substances (for instance, organic or inorganic nitrates, nitrites, S-nitroso, N-nitroso or O-nitroso compounds, NO-chelating substances) either on their own or in various combinations which, in pure form or dissolved in various solvents, can release NO in a catalyzed or non-catalyzed, physically initiated and/or chemical and/or enzymatic reaction in the NO-generating unit, whereby said NO can then be fed by means of the above-mentioned pumping equipment or even without circulation equipment directly or indirectly into the volume of the bathing solution of the volume unit.

In a preferred manner, the replaceable filling container that can be placed into the NO-generating unit and/or into the volume unit can be a cartridge. Suitably, this cartridge contains a pulverulent, gel-like or liquid composition comprising NOD, a buffering substance, an antioxidant and optionally a solvent.

The advantage of the use of such replaceable or exchangeable filling containers is that, by filling them with reactive agents in different combinations and concentrations, the NO-generating unit fitted with such filling containers could generate NO release patterns in the bathing solutions which are varied, characteristic as well as application-specific and treatment-specific in terms of their length and concentration. Therefore, through the selection of a filling container that is specifically filled and inserted into the NO-generating unit, the NO release patterns or concentration patterns in the bathing solutions allow an optimization of the application in terms of adapting it to the technical competence and level of responsibility of the end user. Regarding the filling of the filling containers, the amounts of NO donors (e.g. nitrite or S-nitrosothiols) selected are such that, after the substance in question has dissolved in the bathing solution, final concentrations of preferably 0.001 mM to 10,000 mM, particularly 0.01 mM to 6000 mM, particularly preferably 0.1 mM to 5000 mM, especially 0.4 mM to 2000 mM, very especially 0.5 mM to 1500 mM can be obtained.

The generation of NO in the NO-generating unit of the device according to the invention is preferably regulated through the manipulation of several setting parameters. Such setting parameters include the concentration of NO-releasing agents employed, the strength of the electromagnetic radiation and the properties of the additional physical and/or chemical induction quantities that are responsible for the release of NO from the agents. Moreover, the following parameters can be varied and employed, either individually or in different combinations, as possible induction quantities of an NO release for potentially NO-generating substances:
  the pH value,
  the redox status (the presence of reducing or oxidizing substances).
  the temperature,
  the current flow and/or the voltage;
  the surrounding pressure,
  the intensity of the electromagnetic radiation and the duration of the exposure to which the bathing solution is subjected in the NO-generating unit,
  the surface exposed to the radiation,
  the duration of action of an induction quantity on the NO-releasing agents,
  the flow rate of the bathing solution through the NO-generating unit,
  the distance between the source of electromagnetic radiation and the reaction solution,
  the spectrum of the source of electromagnetic radiation,
  the absorption, transmission and reflection properties of the bathing solution,
  or the concentration of biological or chemical catalysts or mediators which, even outside of the "typical" physical-chemical conditions needed for an optimal NO release, allow NO to be released from NO-generating substances through catalysis or through appropriate acceptor properties (for instance, by means of chromophores and other substances with which, for example, even electromagnetic radiation that is outside of the UVA spectrum could be capable of enabling the release of NO from the appertaining NO-forming agents).

Regarding the latter point, it should be pointed out that, especially in the presence of ions of transition metals such as, for example, $Cu^{2+}$, aqueous nitrite solutions can absorb light at considerably longer wavelengths than pure nitrite solutions can, and therefore the nitrite ion could also be cleaved by light at the wavelengths of 400 nm to 450 nm and also at other wavelengths ≥450 nm, thereby releasing NO. It also applies that, due to a relatively weak binding energy between NO and the remaining molecule, S-nitrosated and N-nitrosated chemical compounds likewise can be photolytically cleaved by means of electromagnetic radiation ≥400 nm, thereby releasing NO.

However, as an alternative, the device according to the invention can be constructed in such a way that the NO-generating unit with its characteristic functions can be completely dispensed with, and the physical/chemical device needed to generate NO, for instance, the light source with the above-mentioned properties, is an integral part of the volume unit, as a result of which the bathing solutions containing NO are generated directly in the volume unit and do not require any circulation through the irradiated volume of an NO-generating unit. Consequently, the source of radiation provided, for example, for the photolytic decomposition can be installed inside and/or outside of the volume unit in such a way that the flow of radiation through the volume unit along with the reaction substances that release the nitric oxide is maximal or optimal for the envisaged application with an eye towards an induced substance decomposition or towards the release of nitric oxide. The volume unit is filled with photolabile NO derivatives, either by adding them directly to the bathing solution, or else by releasing them from a filling container associated with the volume unit.

Here, too, the source of radiation associated with the volume unit preferably emits electromagnetic radiation with wavelengths ranging from 100 nm to 2000 nm or electromagnetic radiation of any other wavelength which, either on its own or with the support of chemical, physical or biological methods, induces cleavage of nitric oxide donors and thus can induce the release of nitric oxide.

The volume unit is made of a material which does not influence the properties of the energy of a source of electromagnetic radiation that is needed for an optimal release of nitric oxide, or which, owing to its properties, in the first place, creates or optimizes the light properties needed for a light-induced release of nitric oxide, or which in the case of pH-dependent NO generation, promotes and optimizes the pH-induced nitrite decomposition. By fitting a volume unit with replaceable or exchangeable filling containers that can be filled with agents in different combinations and concentrations, the volume unit can generate NO release patterns in the bathing solutions which are varied, characteristic as well as application-specific and treatment-specific in terms of their length and concentration. Therefore, through the selection of a specifically filled replaceable or exchangeable filling container that can be inserted into the volume unit, the NO release patterns in the bathing solutions allow an optimization or adaptation to the technical competence and level of responsibility of the end user.

For practical reasons, preference can be given to the use of an aqueous solution from a nitrite source in the volume unit whose concentration preferably ranges from 0.001 mM to 10,000 mM, particularly 0.01 mM to 6000 mM, particularly preferably 0.1 mM to 5000 mM, especially 0.4 mM to 2000 mM, very especially 0.5 mM to 1500 mM.

In an alternative embodiment, the nitrite source in the aqueous solution of the volume unit preferably has a concentration ranging from 100 µM to 5000 mM, particularly preferred from 500 µM to 100 mM, and especially ranging from 1 mM to 10 mM.

In addition, for practical reasons, the use of an aqueous solution containing individual substances or else substance mixtures from the chemical family of the nitroso compounds (R—NO) can likewise be preferred whose concentrations preferably range from 0.001 mM to 10,000 mM, particularly 0.01 mM to 6000 mM, particularly preferably 0.1 mM to 5000 mM, especially 0.4 mM to 2000 mM, very especially 0.5 mM to 1500 mM.

In an alternative embodiment, the substances or else the substance mixtures from the chemical family of the nitroso compounds (R—NO) in the aqueous solution of the volume unit preferably have a concentration ranging from 100 µM to 5000 mM, particularly preferably from 500 µM to 2000 mM and especially between 10 mM and 500 mM.

Depending on the desired or requisite level of concentration of the NO gas dissolved in the bathing solution and depending on the desired or requisite duration for which the specific NO content is kept in the bathing solution, NO-generating solid substances in a specific quantity or solutions with nitrite salts or with the other above-mentioned NO-generating substances can be used in the volume unit in the desired or envisaged concentrations in order to photolytically induce NO generation.

The generation of NO in the volume unit can preferably be regulated through the manipulation of technical, chemical and physical setting parameters. Such setting parameters include the concentration of the NO-releasing agents employed, the strength of the electromagnetic radiation and the properties of the additional physical and/or chemical induction quantities that are responsible for the NO release from the agents. In this context, parameters can be varied and used either individually or else in different combinations, as induction quantities of an NO release from potentially NO-generating substances, for instance, the pH value of the bathing solution, the redox status of the bathing solution (the presence of reducing or oxidizing substances), the temperature of the bathing solution, the surrounding pressure, the intensity of the electromagnetic radiation and the duration of exposure to which the bathing solution is subjected, the surface area exposed to radiation, the duration of action of an induction quantity on the NO-releasing agents, the flow rate of the bathing solution in the volume unit, the distance between the source of electromagnetic radiation and the reaction solution, the spectrum of the source of electromagnetic radiation, the absorption, transmission and reflection properties of the bathing solution, the concentration of biological or chemical catalysts or mediators which, even outside of the "typical" physical-chemical conditions needed for an optimal NO release, nevertheless allow NO to be released from NO-generating substances through catalysis or through appropriate acceptor properties (for instance, by means of chromophores and other substances with which, for example, even electromagnetic radiation that is outside of the UVA spectrum could be capable of enabling the release of NO from the appertaining NO-forming agents).

Regarding the above-mentioned manipulated quantities for the device according to the invention, in case of an induction quantity that is kept constant, varying amounts of nitric oxide could be produced and dissolved in the solution by using varying concentrations of the substances that release nitric oxide. On the other hand, in the case of a constant concentration of the substance that releases nitric oxide, the release of nitric oxide in the bathing solution can be changed by varying the setting parameters of the appertaining induction quantity.

It is known that NO can be dissolved in aqueous solutions up to a concentration of approximately 2 mM before it could escape from the solution into the ambient air. In order to raise the solution concentration and/or the useful life of NO in an aqueous bathing solution as well as in order to increase the solubility behavior of NO in the bathing solution, before or during their use, the bathing solutions can be saturated with inert gases such as, for instance, nitrogen ($N_2$), helium (He) or argon (Ar). For this purpose, the device according to the invention can additionally have an integrated or an external apparatus through which the bathing solution can be conveyed as needed and can be mixed, enriched and/or saturated with an inert gas.

Accordingly, in one embodiment of the invention, the carrier medium is enriched with inert gases, preferably with nitrogen, helium or argon.

In a preferred embodiment, the NO concentration of the carrier medium is a function of the maximum solubility of the NO. This means that all of the NO is present as dissolved NO, and NO is not released, for example, in the form of NO gas bubbles. Aside from the unnecessary contamination of the environment by released NO gas, it has also been found that it is difficult to dissolve gaseous NO back into the carrier medium.

The maximum solubility of NO in an aqueous medium is between 0.2 mM and 5 mM, depending on the temperature, on the pH value and on the other components.

At this juncture, it should be pointed out that the solvent medium used as the carrier for the NO in the device according to the invention does not necessarily have to be an aqueous solution, but rather, it can be any other organic or inorganic, liquid, viscous to gel-like carrier medium that is capable of storing, picking up, dissolving and ultimately releasing NO again.

Owing to the physiological role that NO plays in the stimulation of the metabolism of tissues by means of external application, the solutions containing NO, for example, bathing solutions, generated using the device according to the invention described here can be employed in the field of dermatology for the treatment of surgical or accident-related wounds, chronic, non-healing or poorly healing wounds and/or wounds infested with bacteria as well as for the treatment of dermatological diseases from the spectrum of inflammatory, immunologically regulated or autoimmune diseases. Examples of possible areas of application are:
 stimulation of the metabolism of tissues by means of external application in humans and animals,
 treatment of diabetic feet and wounds,
 treatment of neuropathic pain in cases of diabetes and other diseases,
 treatment of varicose veins,
 treatment of local superficial as well as deep ischemias and thrombopathic diseases of tissues,
 acute and chronic inflammation of the skin,
 skin allergies,
 parasitic infection of the skin,
 atopic dermatitis, especially neurodermitis,
 dermatomyositis,
 *Pemphigus vulgaris* and/or other local and systemic infections and/or acute and chronic inflammatory states, wound defects, such as chronic diabetic-neuropathic *Ulcus*,
*Ulcus* cruris,
decubitus wounds,
infected wounds healing by second intention,
irritation-free wounds healing by first intention, particularly ablative lacerations or abrasions,
(skin) transplants,
treatment of diabetic pain in the lower extremities (foot or leg); and
treatment of poorly perfused skin flap plastic surgeries.

In another aspect, the invention puts forward a method for the treatment of patients that comprises the following steps:
a) generating a carrier medium enriched with NO using an immersion device according to the invention; and
b) immersing parts of the trunk, parts of the extremities or the entire body of a patient into the carrier medium of the immersion device.

In a preferred embodiment of this method, the treatment has been selected from the group encompassing:
stimulation of the metabolism of tissues in humans and animals by means of external application;
treatment of surgical or accident-related wounds;
treatment of chronic, non-healing or poorly healing wounds;
treatment of wounds infested with bacteria and/or fungi;
treatment of dermatological diseases from the spectrum of inflammatory, immunologically regulated or autoimmune diseases;
treatment of diabetic feet and wounds;
treatment of neuropathic pain;
treatment of varicose veins;
treatment of local superficial as well as deep ischemias and thrombopathic diseases of the tissues;
treatment of acute and chronic inflammation of the skin;
treatment of skin allergies;
treatment of parasitic infections of the skin;
treatment of atopic dermatitis, especially neurodermitis, dermatomyositis and *Pemphigus vulgaris*;
treatment of wound defects, such as chronic diabetic-neuropathic *Ulcus, Ulcus cruris*, decubitus wounds;
treatment of large areas of the body for the therapy of systemic diseases such as, for example, high blood pressure (hypertonia) and related hemodynamic diseases;
treatment of patients with (skin) transplants;
treatment of diabetic pain in the lower extremities (foot or leg); and
treatment of poorly perfused skin flap plastic surgeries.

In a preferred embodiment, the method is employed for the treatment of chronic wounds in the lower extremities of diabetic patients.

Advantageously, the method according to the invention is characterized in that the treatment consisting of immersing the entire body, part of the trunk or part of an extremity can last anywhere between a few seconds and many hours.

In a preferred manner, the method entails that the treatment involves immersing the entire body, part of the trunk or part of an extremity in the carrier medium for 5 to 30 minutes, preferably for 7.5 to 20 minutes and especially preferred for 10 to 15 minutes.

In an especially preferred embodiment, the immersion device according to the invention is used to treat chronic wounds of the lower extremities, and here especially in diabetic patients. In this context, the treatment, as a form of prophylaxis, can reduce the risk of the occurrence of chronic wounds as well as the number of medical amputations. This goes hand in hand with a reduction in neuropathic leg pain and with the creation of an improved wound environment, translating into a noticeably improved quantity of life for the patient. Moreover, shortening the time needed for wound care means that a significant lowering of the treatment costs can be anticipated.

In one embodiment of the invention, the immersion device is employed for the therapy of poorly healing wounds. Impaired arterial perfusion and/or venous backflow disorders are major causes for the occurrence as well as the chronicity of wounds in the lower extremities. NO-induced arterial vasodilation improves the perfusion of the affected tissue and, due to the antithrombogenic action of NO, considerably promotes or facilitates venous backflow of the blood. The NO-dependent improvement of these two hemodynamic parameters constitutes the decisive therapy-relevant aspect of a local as well as systemic effect that significantly reduces the risk of the occurrence of wounds or that considerably accelerates their healing. Consequently, the NO that is conveyed to the entire body, to the part of the extremity or to the part of the trunk that is to be treated by means of the immersion device via the carrier medium (immersion medium) can be successfully employed for the therapy of wounds that are difficult to heal.

In a special embodiment, the immersion device according to the invention is used for the treatment of diabetic pain in the lower extremities, in other words, the foot and/or leg. Diabetic pain is a frequent occurrence over the course of diabetes. Diabetic foot or leg pain stems from prolonged elevated concentrations of glucose in the blood, which is the underlying cause of the nerve and vessel damage observed in diabetes. An NO-related arterial vasodilation improves the perfusion of the affected tissue and helps to influence the dissipation of pain with an eye towards pain reduction. Therefore, the NO that is conveyed from the outside along with the carrier medium (immersion medium) to the foot and/or leg can be utilized successfully for the therapy of diabetic foot or leg pain.

In a special embodiment of the invention, the immersion device according to the invention is employed to treat patients with (skin) transplants, here especially for the treatment of poorly perfused skin flap plastic surgery. The two above-mentioned hemodynamic parameters, namely, arterial perfusion and venous backflow, constitute essential parameters for the therapeutic success of skin flap plastic surgery. The expression skin flap plastic surgery refers to techniques in plastic surgery that graft skin and/or tissue from a (dispensable) site to a new, desired site in the same individual. As a rule, these are purely skin flaps, although any tissue, with or without skin, can be transplanted with a pedicle (in other words, with its appertaining blood-supplying vessels and nerves) as well as free (that is to say, with a connection of the blood vessels to the source of blood of the new location). The functional acceptance of the transplanted tissue here is exclusively dependent on the arterial blood supply as well as on a regulated venous drainage. NO-induced arterial vasodilation improves perfusion and thus the requisite supply in skin flap plastic surgery, while the antithrombogenic effect of NO promotes and facilitates venous drainage or backflow of the blood. Therefore, NO preparations used from the outside can ensure or promote the success of a therapy option based on skin flap plastic surgery.

Moreover, by treating larger areas of the body, it might also be possible to address systemic diseases such as, for instance, high blood pressure (hypertonia) and related hemodynamic diseases.

Furthermore, the device according to the invention can also be employed to generate NO-saturated liquids that can be used systemically, for example, to treat high blood pressure; it can be used for the production of nitrosated carriers that spontaneously release NO once again and, for instance, atopically within the scope of dermatological therapies as well as for the production of different NO-binding substances (e.g. NO donors).

Therefore, liquids, gels or solid substances such as carrier, binding or transport media can be employed for the NO with the device according to the invention. It is conceivable to use liquids saturated with NO gas such as, for instance, buffers, solutions, media, serums or blood as the carrier medium and to employ them locally, for example, within the scope of a therapy, or to convey them systemically into the circulatory system, or else to atopically use NO-saturated, viscous carrier media such as gels in order to treat wounds.

For treatment purposes, areas or objects that are to be treated are immersed into the bathing solution for the appropriate period of time of treatment, which can vary between a few seconds and many hours. In order to improve the mixing of the bathing solution, the device according to the invention can have circulation equipment that can be integrated into the device as a whole or else installed externally. The immersion procedure here is preferably done using a volume unit that is open towards the top, whereby, as an alternative, the upper opening can be sealed off with a gasket or a cover whereby, however, it should nevertheless be possible to insert an object through the seal.

With an eye towards reducing, avoiding or preventing contamination of the ambient air with NO or with its oxidative reaction products, the volume unit with the variant that is open towards the top can have an apparatus that generates a continuous, slight air flow above the bathing solution, said air flow being continuously suctioned off and passed through an activated carbon filter or through some other means that is capable of neutralizing or eliminating reactive gas species. On the basis of this notion, the variant of the volume unit that is sealed off towards the top can have an appropriate apparatus that continuously suctions off the gas volume above the bathing solution and likewise conveys it through an activated carbon filter or conveys it to the outside through some other means. In this manner, it is possible to ensure a continuous inactivation of reactive nitrogen oxide species. The activated carbon filter provided for this purpose or any other technical apparatus of this sort can be a replaceable or exchangeable unit of the volume unit. In order to ensure safe use of the device according to the invention, the device has an electronically controlled, application-specific program selection, including a safety switch-OFF for the device, as well as appropriate sensors for NO, $NO_2$, temperature and safety as well as a remote control and the capability to be connected to external control and documentation units or applications. The safety management measures also include the electronically controlled application-specific and user-specific monitoring of the replaceable or exchangeable filling containers that are specifically filled as well as of the circulation equipment or filtering means.

In one special aspect, the invention puts forward the following embodiments:

Embodiment 1: a device for purpose of immersing objects, characterized in that, through a cleavage of chemical nitric oxide donors (hereinafter referred to as NO donors) induced in the device by physical stimuli, a medium (immersion medium) that is suitable for the immersion of objects can be enriched with nitric oxide (NO) and it can then be used for medical as well as technical purposes.

Embodiment 2: the device according to embodiment 1, characterized in that the device consists of a volume unit which can hold any desired volume of an immersion medium and which is associated with an NO-generating unit that serves to enrich the immersion medium of the volume unit with NO.

Embodiment 3: the device according to embodiments 1 and 2, characterized in that the NO-generating unit can likewise hold any desired volume content and it is in communication with the volume of the volume unit, whereby the content of the volume unit—which is preferably an aqueous solution but which can also be any organic or inorganic liquid, viscous to gel-like or solid carrier medium that is capable of dissolving, binding, storing as well as releasing NO donors or NO—can be conveyed by means of circulation or pumping equipment through the volume chamber of the NO-generating unit and then back into the volume unit of the device that holds the volume.

Embodiment 4: the device according to embodiments 1 to 3, characterized in that the volume content of the NO-generating unit can be exposed to an electrolytic and/or thermolytic and/or electromagnetic and/or some other physical or chemical stimulus, preferably, however, to radiation emitted by a source of electromagnetic radiation, whereby the source of radiation can be a glow-discharge or gas-discharge lamp (low-pressure discharging or high-pressure discharging) coated with appropriate fluorochromes, light-emitting diodes (LED), organic light-emitting diodes (OLED), lasers or any other source of electromagnetic radiation that is able to induce the cleavage of NO donors and thus the release of NO from the appertaining chemical precursors or substrates, either on its own or else with the assistance of chemical or physical methods in a non-catalyzed manner or else within the scope of a catalyzed reaction, for instance, by means of ions of transition metals such as, for example, $Cu^{2-}$ ions.

Embodiment 5: the device according to embodiments 1 to 4, characterized in that the NO donors that are needed for the NO production (e.g. organic or inorganic nitrates, nitrites, sulfur-nitroso, nitrogen-nitroso or oxygen-nitroso compounds, NO-metal compounds, NO-chelating substances, etc.) and that are in the volume medium of the volume unit can be added by means of the circulation or pumping equipment of the NO-generating unit for cleavage purposes, or, as an alternative to this, a replaceable or exchangeable cartridge or filling container (hereinafter referred to as a replaceable filling container) can be inserted into the NO-generating unit, said filling container containing NO donors and other substances in any desired concentration and combination from which NO can be released in the NO-generating unit, and the NO can then be introduced in gas form or in dissolved form into the volume unit that contains the volume of immersion medium, as a result of which, due to the specific filling of the replaceable filling container or NO-generating unit, NO release patterns can be generated in the immersion media, which are varied, characteristic and application-specific as well as treatment-specific in terms of their length and concentration.

Embodiment 6: the device according to embodiments 1 to 5, characterized in that, before or during use, the carrier media with the NO dissolved therein can be saturated with inert gases that are not reactive for NO such as, for example, nitrogen ($N_2$), helium (He), argon (Ar) using an additional sub-unit for purposes of improving the solubility behavior of the solvent media vis-à-vis the generated NO as well as in order to increase the useful life of the dissolved NO in the solvent medium.

Embodiment 7: the device according to embodiments 1 to 6, characterized in that the device has an autonomous, electronically regulated safety management system which comprises 1) an electronically controlled, application-specific program selection as well as a safety switch-OFF, 2) the NO generation can be safely regulated, preferably by manipulating relevant technical, chemical and physical setting parameters using sensors to detect the temperature, pressure, NO concentration, nitrogen dioxide ($NO_2$) concentration as well as other safety-relevant parameters, 3) the application-specific and user-specific as well as the electronically controlled detection and utilization acceptance of the specifically filled filling containers as well as the optionally replaceable circulation and pumping equipment, and 4) an electronically controlled detection and utilization acceptance of a replaceable filtering means that is integrated into the device and that serves to eliminate gases that might be harmful to health.

Embodiment 8: the device according to embodiments 1 to 7, characterized in that the device has the capability of being remotely controlled as well as of being connected to external control and documentation units or applications.

Embodiment 9: the device according to embodiments 1 to 8, characterized in that it can be employed to stimulate the metabolism of tissues through external use in humans or animals in the field of dermatology and surgery for the treatment of surgical or accident-related wounds, chronic, non-healing or poorly wounds healing and/or wounds infested with bacteria or fungi as well as for the treatment of dermatological diseases from the spectrum of inflammatory, immunologically regulated or autoimmune diseases, for instance, in the treatment of diabetic feet and wounds, neuropathic pain in diabetic patients as well as other diseases ranging from varicose veins, local superficial as well as deep ischemias and thrombopathic diseases of tissues, acute and chronic inflammation of the skin, skin allergies, parasitic infections of the skin, atopic dermatitis, especially neurodermititis, dermatomyositis, *Pemphigus vulgaris* and/or other local and systemic infections and/or acute and chronic inflammatory states, (skin) transplants, wound defects, such as chronic diabetic-neuropathic *Ulcus, Ulcus cruris*, decubitus wounds, infected wounds healing by second intention, irritation-free, wounds healing by first intention, particularly such as ablative lacerations or abrasions, but also for the treatment of larger areas of the body in the therapy of systemic diseases such as, for instance, high blood pressure (hypertonia) and related hemodynamic diseases, whereby such a treatment can individually last between a few seconds and many hours.

EXAMPLES

1. Generation of NO by Means of the Device According to the Invention

The NO-generating unit contained tap water, buffer salts (8 g/l NaCl+0.2 g/l KCl+1.424 g/l $Na_2HPO_4$+0.2 g/l $KH_2PO_4$, pH=7.0), 1.45 mM $NaNO_2$ and 10 mM Na ascorbate.

UV radiation of this solution containing nitrite yielded a solution that contained approximately 150 µM NO. The stability of the generated NO and the occurrence of oxidation products were analyzed on the basis of this solution. Moreover, the effect in terms of perfusion and erythema formation was tested within the scope of its use as a foot bath.

1.1 Stability Test

This solution first underwent a stability test, that is to say, it was ascertained how the content of NO changes over a time span of 20 minutes. Every two minutes an aliquot of 10 ml of the bathing solution was pipetted into a flask (volume capacity of 175 ml) through which helium gas was flowing (100 ml/min) and which had already been filled with 40 ml of a PBS solution (pH of 7.4). During the entire procedure, the helium-gas mixtures escaping from the flask were conveyed directly into an NO analysis unit (Chemiluminescence Detector—CLD 822 Sr made by Eco Physics of Duernten, Switzerland) which detected and recorded the NO amounts in ppm (parts per million) that were contained in the gas mixture (in this context, also see Opländer et al. 2010—Nitric Oxide—Bio. Ch. 23: 275-283). The measured results are shown in FIG. 1A. It was found that the NO content was virtually constant over the time span of 20 minutes, it dropped by about 10%, which was not statistically significant.

1.2. Generation of Oxidation Products

Using the solution described above, parallel to the above-mentioned NO detection, the amount of nitrogen dioxide radicals, as the most important oxidation product of NO, was detected during the same measurement. Here, very low concentrations of $NO_2$ within the range of 1.5 ppm occurred only after 10 minutes, and these concentrations rose only negligibly up until the maximum time value of 20 minutes. The measured $NO_2$ values, however, were not significantly higher than the initial values (see FIG. 1B).

1.3 Use as a Foot Bath

One foot of a volunteer test subject was immersed into the solution described above (27° C. [80.6° F.]), which contained a constant amount of NO, and was left in this foot bath for a total of 10 minutes. During the foot bath, the solution was carefully stirred by slight movement of the immersed foot. During this 10-minute exposure time as well as over the subsequent 15 minutes, the foot was analyzed in terms of the skin perfusion at a tissue depth of 1 mm to 2 mm and 6 mm to 8 mm. The foot was also checked for the formation of erythema.

1.3.1 Dermal Perfusion

A significant rise in perfusion was observed at both skin depths after the 10-minute exposure in the NO foot bath (see FIGS. 2A and 2B), which then returned to the level of the control values over a time span of 10 to 15 minutes. It was also possible to see the increased skin perfusion with the naked eye on the basis of the formation of a temporary erythema (see FIG. 3).

FIGURES

Figure 3:
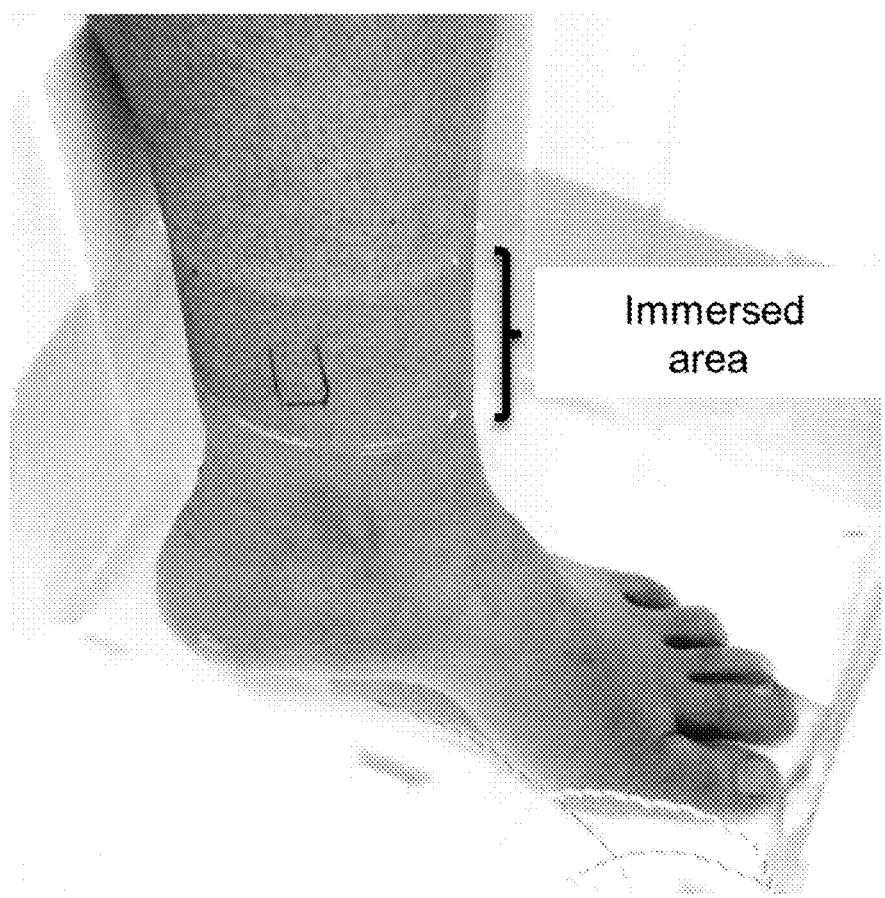
Figure 4:
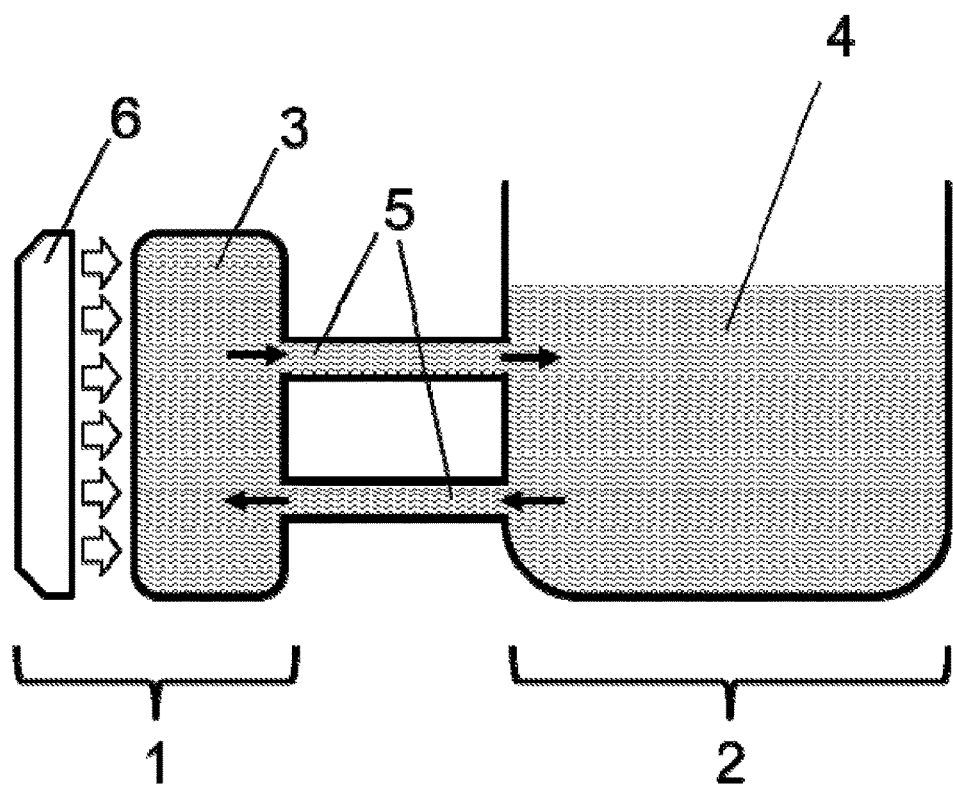

The invention will be described in greater detail bellow on the basis of the figures, without this constituting a restriction of the invention. The following is shown:

FIG. 1A: the result of a stability measurement of a buffer aqueous solution containing NO in accordance with Example 1 over a time span of 20 minutes. The value is shown as a percentage (%) relative to the original NO content;

FIG. 1B: the result of an analysis of the oxidation product $NO_2^-$ in an NO-containing buffer aqueous solution according to Example 1 over a time span of 20 minutes. The $NO_2^-$ is indicated in parts per million (ppm);

FIG. 2: the determination of the skin perfusion during a 10-minute exposure by immersing the foot into a foot bath containing NO and after a subsequent time span of 15 minutes (see Example 1). The relative ratio of the perfusion is shown in an arbitrary unit (AU) at a tissue depth of 1 mm to 2 mm (A) as well as at a tissue depth of 6 mm to 8 mm (B). In this context, the foot was bathed either in a buffer solution containing NO (white squares) or in a corresponding buffer solution (black diamonds) as the control, and the perfusion was detected non-invasively using a flat probe and an O2C-Doppler spectroscopic detection system (LEA-Medizintechnik GmbH, Giessen, Germany) at the indicated points in time;

FIG. 3: the confirmation of increased skin perfusion on the basis of (temporary) erythema formation after the 10-minute exposure of the foot in a foot bath containing NO. The photo clearly shows that, because of the greater perfusion, the foot is very reddened in the area that has been immersed;

FIG. 4: the schematic depiction of the cross section of an immersion device with the NO-generating unit (1) and with the volume unit (2), which are connected to each other by means of two connection pipes (5). The volume unit, which is open towards the top, contains an immersion medium (4) for purposes of immersing objects. The NO-generating unit comprises a volume chamber with a carrier medium (3) that is irradiated by a source of UV radiation (6).

Figure 5:
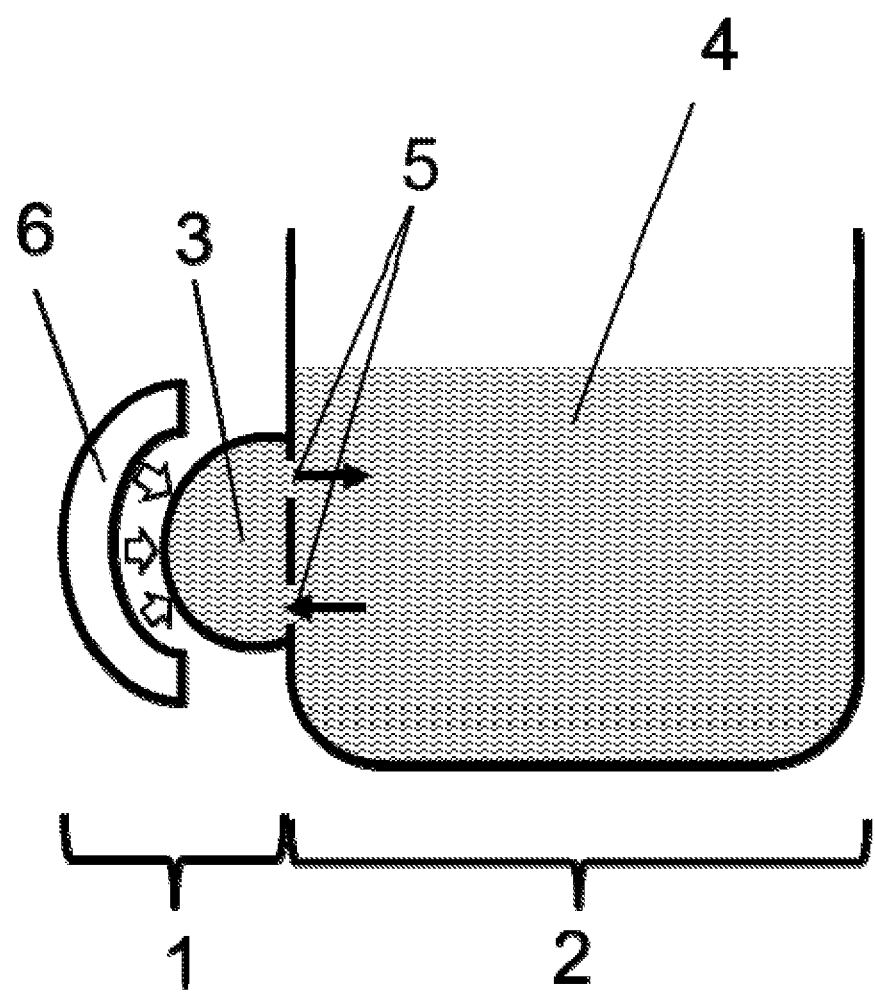

FIG. 5: the schematic depiction of the cross section of an immersion device with the NO-generating unit (1) and with the volume unit (2), whereby the NO-generating unit is attached directly to the volume unit and these two compartments are connected via two openings (5). The volume unit, which is open towards the top, contains an immersion medium (4) for purposes of immersing objects. The NO-generating unit comprises a volume chamber with a carrier medium (3) that is irradiated by a source (6) of UV radiation.

Figure 6:
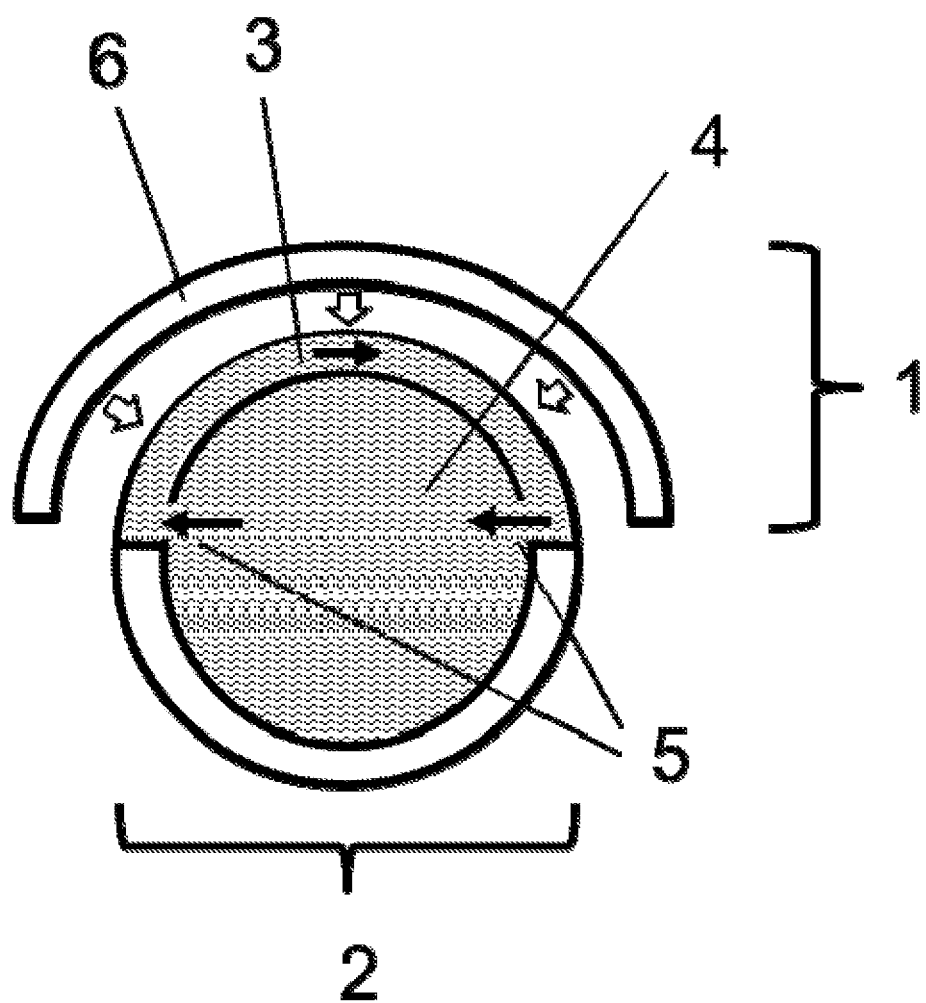

FIG. 6: the schematic depiction of the cross section of an immersion device with the NO-generating unit (1) and with the volume unit (2), whereby the NO-generating unit and the volume unit are arranged inside a circular vessel and the NO-generating unit is separated from the volume unit as the external segment. Here, the NO-generating unit is connected to the volume unit via two openings (5). The volume unit, as an internal area of the circular vessel, is filled with the immersion medium (4) so that objects can be immersed. The carrier medium (3) contained in the volume chamber of the NO-generating unit is irradiated by a curved source (6) of UV radiation located on the outside.

LITERATURE

[1] K. D. Kröncke, K. Fehsel, and V. Kolb-Bachofen, Inducible nitric oxide synthase in human diseases. *Clin Exp Immunol* 113 (1998) 147-56.

[2] K. Matsunaga, and R. F. Furchgott, Responses of rabbit aorta to nitric oxide and superoxide generated by ultraviolet irradiation of solutions containing inorganic nitrite. *J Pharmacol Exp Ther* 259 (1991) 1140-6.

[3] M. Fischer, and P. Warneck, Photodecomposition of nitrite and undissociated nitrous acid in aqueous solution. *J. Phys. Chem.* 100 (1996) 18749-18756.

[4] H. Strehlow, and I. Wagner, Flash photolysis in aqueous nitrite solutions. *Z. Phys. Chem. NF* 132 (1982) 151-160.

[5] S. Frank, H. Kampfer, C. Wetzler, and J. Pfeilschifter, Nitric oxide drives skin repair: novel functions of an established mediator. *Kidney Int* 61 (2002) 882-8.

[6] S. Frank, B. Stallmeyer, H. Kampfer, N. Kolb, and J. Pfeilschifter, Nitric oxide triggers enhanced induction of vascular endothelial growth factor expression in cultured keratinocytes (HaCaT) and during cutaneous wound repair. *Faseb J* 13 (1999) 2002-14.

[7] S. Frank, H. Kampfer, M. Podda, R. Kaufmann, and J. Pfeilschifter, Identification of copper/zinc superoxide dismutase as a nitric oxide-regulated gene in human (HaCaT) keratinocytes: implications for keratinocyte proliferation. *Biochem J* 346 Pt 3 (2000) 719-28.

[8] K. Yamasaki, H. D. Edington, C. McClosky, E. Tzeng, A. Lizonova, I. Kovesdi, D. L. Steed, and T. R. Billiar, Reversal of impaired wound repair in iNOS-deficient mice by topical adenoviral-mediated iNOS gene transfer. *J Clin Invest* 101 (1998) 967-71.

[9] J. Pfeilschifter, W. Eberhardt, and A. Huwiler, Nitric oxide and mechanisms of redox signalling: matrix and matrix-metabolizing enzymes as prime nitric oxide targets. *Eur J Pharmacol* 429 (2001) 279-86.

[10] Y. Ishii, T. Ogura, M. Tatemichi, H. Fujisawa, F. Otsuka, and H. Esumi, Induction of matrix metalloproteinase gene transcription by nitric oxide and mechanisms of MMP-1 gene induction in human melanoma cell lines. *Int J Cancer* 103 (2003) 161-8.

[11] M. B. Witte, F. J. Thornton, D. T. Efron, and A. Barbul, Enhancement of fibroblast collagen synthesis by nitric oxide. *Nitric Oxide* 4 (2000) 572-82.

[12] F. Verrecchia, and A. Mauviel, TGF-beta and TNF-alpha: antagonistic cytokines controlling type I collagen gene expression. *Cell Signal* 16 (2004) 873-80.

[13] D. A. Siwik, and W. S. Colucci, Regulation of matrix metalloproteinases by cytokines and reactive oxygen/nitrogen species in the myocardium. *Heart Fail Rev* 9 (2004) 43-51.

[14] V. M. Darley-Usmar, R. P. Patel, V. B. O'Donnell, and B. A. Freeman, Antioxidant actions of nitric oxide. in: L. J. Ignarro, (Ed.), Nitric Oxide: Biology and Pathobiology, Academic Press, San Diego, (2000), pp. 265-276.

[15] S. P. Goss, B. Kalyanaraman, and N. Hogg, Antioxidant effects of nitric oxide and nitric oxide donor compounds on low-density lipoprotein oxidation. *Methods Enzymol* 301 (1999) 444-53.

[16] D. A. Wink, J. A. Cook, R. Pacelli, J. Liebmann, M. C. Krishna, and J. B. Mitchell, Nitric oxide (NO) protects against cellular damage by reactive oxygen species. *Toxicol Lett* 82-83 (1995) 221-6.

[17] B. Brune, A. von Knethen, and K. B. Sandau, Nitric oxide (NO): an effector of apoptosis. *Cell Death Differ* 6 (1999) 969-75.

[18] D. Moellering, J. McAndrew, R. P. Patel, T. Cornwell, T. Lincoln, X. Cao, J. L. Messina, H. J. Forman, H. Jo, and V. M. Darley-Usmar, Nitric oxide-dependent induction of glutathione synthesis through increased expression of gamma-glutamylcysteine synthetase. *Arch Biochem Biophys* 358 (1998) 74-82.

[19] U. Forstermann, M. Nakane, W. R. Tracey, and J. S. Pollock, Isoforms of nitric oxide synthase: functions in the cardiovascular system. *Eur Heart J* 14 Suppl 1 (1993) 10-5.

[20] P. He, M. Zeng, and F. E. Curry, Effect of nitric oxide synthase inhibitors on basal microvessel permeability and endothelial cell [$Ca^{2+}$]i. *Am J Physiol* 273 (1997) H747-55.

[21] M. Toborek, and S. Kaiser, Endothelial cell functions. Relationship to atherogenesis. *Basic Res Cardiol* 94 (1999) 295-314.

[22] M. Kelm, and B. Strauer, Endotheliale Dysfunktion; Therapeutische and prognostische Relevanz [Endothelial dysfunction; therapeutic and prognostic relevance]. *Internist.* 40 (1999) 1300-1307.

[23] T. P. Amadeu, A. B. Seabra, M. G. de Oliveira, and A. M. Costa, S-nitrosoglutathione-containing hydrogel accelerates rat cutaneous wound repair. *J Eur Acad Dermatol Venereol* 21 (2007) 629-37.

[24] R. Weller, and M. J. Finnen, The effects of topical treatment with acidified nitrite on wound healing in normal and diabetic mice. *Nitric Oxide* 15 (2006) 395-9.

[25] A. B. Shekhter, V. A. Serezhenkov, T. G. Rudenko, A. V. Pekshev, and A. F. Vanin, Beneficial effect of gaseous nitric oxide on the healing of skin wounds. *Nitric Oxide* 12 (2005) 210-9.

[26] W. S. McDonald, T. P. Lo, Jr., M. Thurmond, C. Jones, R. Cohen, A. Miller, and D. Beasley, Role of nitric oxide in skin flap delay. *Plast Reconstr Surg* 113 (2004) 927-31.

[27] C. Belge, P. B. Massion, M. Pelat, and J. L. Balligand, Nitric oxide and the heart: update on new paradigms. *Ann NY Acad Sci* 1047 (2005) 173-82.

[28] B. Gaston, Summary: systemic effects of inhaled nitric oxide. *Proc Am Thorac Soc* 3 (2006) 170-2.

[29] T. M. Dawson, and S. H. Snyder, Gases as biological messengers: nitric oxide and carbon monoxide in the brain. *J Neurosci* 14 (1994) 5147-59.

[30] C. C. Miller, M. K. Miller, A. Ghaffari, and B. Kunimoto, Treatment of chronic nonhealing leg ulceration with gaseous nitric oxide: a case study. *J Cutan Med Surg* 8 (2004) 233-8.

[31] A. Ghaffari, D. H. Neil, A. Ardakani, J. Road, A. Ghahary, and C. C. Miller, A direct nitric oxide gas delivery system for bacterial and mammalian cell cultures. *Nitric Oxide* 12 (2005) 129-40.

[32] A. Ghaffari, C. C. Miller, B. McMullin, and A. Ghahary, Potential application of gaseous nitric oxide as a topical antimicrobial agent. *Nitric Oxide* 14 (2006) 21-9.

[33] A. Ghaffari, R. Jalili, M. Ghaffari, C. Miller, and A. Ghahary, Efficacy of gaseous nitric oxide in the treatment of skin and soft tissue infections. *Wound Repair Regen* 15 (2007) 368-77.

[34] Z. S. Galis, and J. J. Khatri, Matrix metalloproteinases in vascular remodeling and atherogenesis: the good, the bad, and the ugly. *Circ Res* 90 (2002) 251-62.

[35] S. C. Tyagi, and M. R. Hayden, Role of nitric oxide in matrix remodeling in diabetes and heart failure. *Heart Fail Rev* 8 (2003) 23-8.

[36] J. Pfeilschifter, W. Eberhardt, and K. F. Beck, Regulation of gene expression by nitric oxide. *Pflugers Arch* 442 (2001) 479-86.

[37] R. Zamora, Y. Vodovotz, K. S. Aulak, P. K. Kim, J. M. Kane, 3rd, L. Alarcon, D J. Stuehr, and T. R. Billiar, A DNA microarray study of nitric oxide-induced genes in mouse hepatocytes: implications for hepatic heme oxygenase-1 expression in ischemia/reperfusion. *Nitric Oxide* 7 (2002) 165-86.

[38] J. Hemish, N. Nakaya, V. Mittal, and G. Enikolopov, Nitric oxide activates diverse signaling pathways to regulate gene expression. *J Biol Chem* 278 (2003) 42321-9.

[39] M. Ziche, L. Morbidelli, E. Masini, S. Amerini, H. J. Granger, C. A. Maggi, P. Geppetti, and F. Ledda, Nitric oxide mediates angiogenesis in vivo and endothelial cell growth and migration in vitro promoted by substance P. *J Clin Invest* 94 (1994) 2036-44.

[40] S. J. Leibovich, P. J. Polverini, T. W. Fong, L. A. Harlow, and A. E. Koch, Production of angiogenic activity by human monocytes requires an L-arginine/nitric oxide-synthase-dependent effector mechanism. *Proc Natl Acad Sci USA* 91 (1994) 4190-4.

[41] N. S. Bryan, B. O. Fernandez, S. M. Bauer, M. F. Garcia-Saura, A. B. Milsom, T. Rassaf, R. E. Maloney, A. Bharti, J. Rodriguez, and M. Feelisch, Nitrite is a signaling molecule and regulator of gene expression in mammalian tissues. *Nature Chemical Biology* 1 (2005) 290-297.

The invention claimed is:

1. An immersion device comprising:
a nitric oxide (NO)-generating unit having a source of UV radiation and a volume chamber for holding a NOD-containing aqueous solution, wherein the NO-generating unit is configured to enrich the NOD-containing aqueous solution held in the volume chamber with NO using UV radiation from the source; and
a volume unit configured to receive objects to be immersed in aqueous solution enriched with NO transferred from the NO-generating unit into the volume unit;
wherein there is an opening toward a top of the volume unit for receiving the objects to be immersed,
wherein the NO-generating unit is sealable,
wherein transfer of the aqueous solution enriched with NO from the NO-generating unit into the volume unit is made through two openings located in a shared wall that connects the NO-generating unit with the volume unit, or is made through two connecting lines,
wherein the immersion device is configured to continuously circulate the aqueous solution on a path that passes from the volume chamber of the NO-generating unit into the volume unit and from the volume unit back into the volume chamber of the NO-generating unit,
wherein the immersion device is provided with a temperature-control unit configured to selectively heat or cool the aqueous solution, and
wherein the source of UV radiation is selected from the group consisting of a glow-discharge lamp (low-pressure discharging or high-pressure discharging) coated with fluorochromes, a gas-discharge lamp (low-pressure discharging or high-pressure discharging) coated with fluorochromes, a light-emitting diode (LED), an organic light-emitting diode (OLED) and a laser.

2. The immersion device according to claim 1, wherein the volume chamber of the NO-generating unit and/or the volume unit is configured to receive, by insertion, a replaceable filling container containing a pulverulent, gel-like or liquid composition containing a NOD, a buffering substance, an antioxidant and optionally a solvent.

3. The immersion device according to claim 2, wherein the replaceable filling container is a cartridge.

4. The immersion device according to claim 1, wherein the volume unit is configured to receive parts of a human trunk, parts of a human extremity or an entire human body for immersion in the aqueous solution.

5. The immersion device according to claim 4, wherein the NO-generating unit is configured to selectively increase or decrease a content of NO in the aqueous solution over a period of time during which the parts of the human trunk, parts of the human extremity or the entire human body are immersed in the aqueous solution.

6. A method for providing treatment to a human comprising:
providing an immersion device according to claim 4; and
immersing at least part of the human in aqueous solution in the volume unit;

wherein, while the at least part of the human is immersed in the aqueous solution in the volume unit, the NO-generating enriches the NOD-containing aqueous solution held in the volume chamber with NO using UV radiation from the source, wherein, while the at least part of the human is immersed in the aqueous solution in the volume unit, the immersion device continuously circulates the aqueous solution on a path that passes from the volume chamber of the NO-generating unit into the volume unit and from the volume unit back into the volume chamber of the NO-generating unit, and wherein the treatment is selected from the group consisting of:
(a) stimulation of metabolism of tissues in humans and animals through external application;
(b) treatment of surgical or accident-related wounds;
(c) treatment of chronic, non-healing or poorly healing wounds;
(d) treatment of wounds infested with bacteria and/or fungi;
(e) treatment of dermatological diseases;
(f) treatment of diabetic feet and wounds;
(g) treatment of neuropathic pain;
(h) treatment of varicose veins;
(i) treatment of local superficial or deep ischemias and thrombopathic diseases of the tissues;
(j) treatment of acute and chronic inflammation of skin;
(k) treatment of skin allergies;
(l) treatment of parasitic infections of the skin;
(m) treatment of atopic dermatitis;
(n) treatment of wound defects;
(o) treatment of high blood pressure (hypertonia) and related hemodynamic diseases;
(p) treatment of patients with skin transplants;
(q) treatment of diabetic pain in lower extremities; and
(r) treatment of poorly perfused skin flap plastic surgeries.

7. A method for treating a chronic wound on a lower extremity of a diabetic patient, the method comprising:
providing an immersion device according to claim 4; and
immersing the lower extremity in aqueous solution in the volume unit;
wherein, while the lower extremity is immersed in the aqueous solution in the volume unit, the NO-generating enriches the NOD-containing aqueous solution held in the volume chamber with NO using UV radiation from the source, and
wherein, while the lower extremity is immersed in the aqueous solution in the volume unit, the immersion device continuously circulates the aqueous solution on a path that passes from the volume chamber of the NO-generating unit into the volume unit and from the volume unit back into the volume chamber of the NO-generating unit.

8. The method according to claim 6 wherein treatment is conducted for a period of 5 to 30 minutes.

9. The method according to claim 6 wherein treatment is conducted for a period of 7.5 to 20 minutes.

10. The method according to claim 6 wherein treatment is conducted for a period of 10 to 15 minutes.

* * * * *